(12) United States Patent
Motoyuki et al.

(10) Patent No.: US 8,426,589 B2
(45) Date of Patent: Apr. 23, 2013

(54) PROCESS FOR PRODUCTION OF QUINAZOLINE DERIVATIVE

(75) Inventors: Hagihara Motoyuki, Amagasaki (JP); Shinomoto Shoji, Matsubara (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 13/141,376

(22) PCT Filed: Dec. 24, 2009

(86) PCT No.: PCT/JP2009/071445
§ 371 (c)(1),
(2), (4) Date: Jun. 22, 2011

(87) PCT Pub. No.: WO2010/074150
PCT Pub. Date: Jul. 1, 2010

(65) Prior Publication Data
US 2011/0257391 A1   Oct. 20, 2011

(30) Foreign Application Priority Data
Dec. 25, 2008   (JP) .................. 2008-330600

(51) Int. Cl.
*C07D 239/00* (2006.01)
*C07D 239/02* (2006.01)

(52) U.S. Cl.
USPC ........................................ 544/242

(58) Field of Classification Search .......... 544/242
See application file for complete search history.

(56) References Cited

U.S. PATENT DOCUMENTS
2009/0143414 A1   6/2009 Kume

FOREIGN PATENT DOCUMENTS
WO   2006/090717      8/2006
WO   WO 2006/090717 *  8/2006

OTHER PUBLICATIONS

Williams et al., Tet. Let., 1995, vol. 36, No. 31, pp. 5461-5464.*
Wallace et al., Tet. Let., 1997, vol. 38, No. 28, pp. 4939-4942.*
Lee et al., Synthetic Comm., 1999, vol. 29, No. 8, pp. 1249-1255.*
International Search Report issued Feb. 9, 2010 in International (PCT) Application No. PCT/JP2009/071445.
J. Michael Williams et al., "A New General Method for Preparation of N-Methoxy-N-Methylamides. Application in Direct Conversion of an Ester to a Ketone", Tetrahedron Letters, vol. 36, No. 31, pp. 5461-5464, 1995.
Owen B. Wallace, "Solid Phase Synthesis of Ketones from Esters", Tetrahedron Letters, vol. 38, No. 28, pp. 4939-4942, 1997.
Na Ra Lee et al., "One-Pot Synthesis of Ketones Using N-Methoxy-N-Methyl-2-Pyridyl Urethane", Synthetic Communications, vol. 29, No. 8, 1249-1255, 1999.
International Preliminary Report on Patentability & Written Opinion of the International Searching Authority (English translation) issued Aug. 9, 2011 in International (PCT) Application No. PCT/JP2009/071445.
T. Yoneda et al., "The Antiproliferative Effects of Tyrosine Kinase Inhibitors Tyrphostins on a Human Squamous Cell Carcinoma in Vitro and in Nude Mice", Cancer Research, vol. 51, pp. 4430-4435, Aug. 15, 1991.
K. B. Reddy et al., "Inhibition of Breast Cancer Cell Growth in Vitro by a Tyrosine Kinase Inhibitor", Cancer Research, vol. 52, pp. 3636-3641, Jul. 1, 1992.
Y. Kokai et al., "Synergistic Interaction of p185c-neu and the EGF Receptor Leads to Transformation of Rodent Fibroblasts", Cell, vol. 58, pp. 287-292, Jul. 28, 1989.
V. G. Brunton et al., "Cell-Signaling Targets for Antitumor Drug Development", Cancer Chemother. and Pharmacol., vol. 32, pp. 1-19, 1993.
Supplementary European Search Report issued Jul. 18, 2012 in corresponding European Application No. 09834948.3.
Dominic J. Reynolds et al., "The synthesis of GW710936X to support the development of potent PPARγ agonists", Tetrahedron, 2001, vol. 57, pp. 7765-7770.

* cited by examiner

*Primary Examiner* — Paul V. Ward
(74) *Attorney, Agent, or Firm* — Wenderoth, Lind & Ponack, L.L.P.

(57) ABSTRACT

A process for preparing a compound (III) is provided, in which the compound (III) is prepared from a methoxycarbonyl derivative through a methoxyamide derivative. These two reaction steps are continuously carried out and substantially the same as one step. The compound (III) is useful as a synthetic intermediate for preparing a dual tyrosine kinase inhibitor and can be conveniently prepared in high yield according to the present invention.

13 Claims, 1 Drawing Sheet

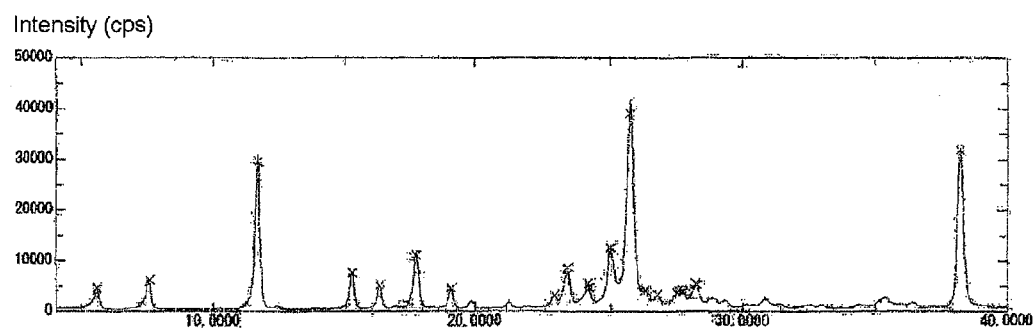

PROCESS FOR PRODUCTION OF QUINAZOLINE DERIVATIVE

TECHNICAL FIELD

The present invention relates to a process for preparing a compound having a 1-oxo-2-butyn-1-yl substituent at 6-position which is useful as a synthetic intermediate of a dual inhibitor of both EGF receptor tyrosine kinase and HER2 tyrosine kinase, and a crystalline form of the said synthetic intermediate.

BACKGROUND ART

Tyrosine kinase is an enzyme which phosphorylates tyrosine residues in substrate proteins, and is known to play an important role in an intracellular signal transduction system concerning cellular differentiation and proliferation. Especially, it is known that a growth factor receptor tyrosine kinase (hereinafter receptor tyrosine kinase) such as HER2 (also called as ErbB2 or Neu) and EGF receptor etc. are considerably involved in cancer development, and their activities are increased in a variety of human cancers (Non-Patent Literature 1, Non-Patent Literature 2 and Non-Patent Literature 3).

Also it is known that co-expression of EGF receptor and HER2 further promotes canceration by EGF receptor alone (Non-Patent Literature 4) and a dual inhibitor that inhibits tyrosine kinase of both EGF receptor and HER2 is advantageous in having superior therapeutic effect in wider range of disease by synergistic effect of dual inhibition when compared with a EGF receptor or a HER2 selective inhibitor. A quinazoline derivative (VI) having a substituent containing an alkoxyimino structure at 6-position:

[Chemical Formula 1]

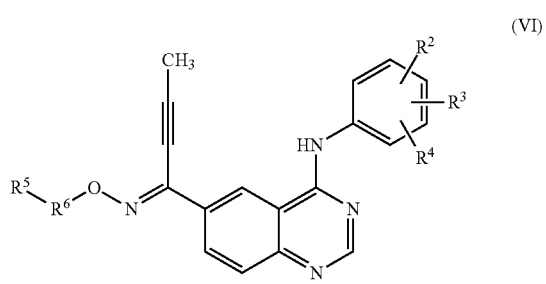

(VI)

wherein $R^2$ is a hydrogen atom, halogen, substituted or unsubstituted alkyloxy, substituted or unsubstituted alkenyloxy, substituted or unsubstituted alkynyloxy or formula: —Y—$R^y$ wherein Y is —O—, —S—, —$SO_2$— or alkylene which may be intervened with —O—, —S— or —N($R^z$)—; and $R^y$ is substituted or unsubstituted aryl or substituted or unsubstituted heteroaryl; $R^z$ is a hydrogen atom, substituted or unsubstituted alkyl, substituted or unsubstituted acyl, substituted or unsubstituted alkyloxycarbonyl, substituted or unsubstituted alkenyloxycarbonyl or substituted or unsubstituted aralkyloxycarbonyl;

$R^3$ and $R^4$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino; $R^5$ is substituted or unsubstituted aryl, substituted or unsubstituted heteroaryl or substituted or unsubstituted heterocyclyl or substituted or unsubstituted amino, and $R^6$ is substituted or unsubstituted C1-3 alkylene, is one of these dual inhibitors and is expected as a novel cancer agent (Patent Literature 1).

A compound (III) having a 1-oxo-2-butyn-1-yl substituent at 6-position:

[Chemical Formula 2]

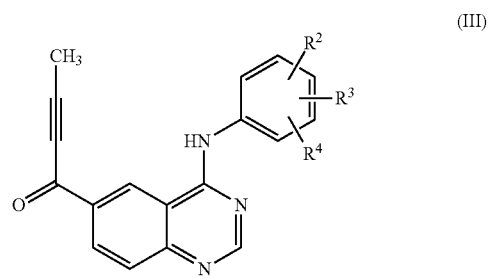

(III)

wherein $R^2$, $R^3$ and $R^4$ are as defined above, is an important synthetic intermediate for preparing a quinazoline derivative (VI), since the above quinazoline derivative (VI) is prepared by reacting a compound (III) with an alkoxyamine derivative.

PRIOR ART

Patent Document(s)

[Patent Literature 1] WO2006/090717

Nonpatent Document(s)

[Non-Patent Literature 1] Cancer Res., 1991, vol. 51, p. 4430-4435

[Non-Patent Literature 2] Cancer Res., 1992, vol. 52, p. 3636-3641

[Non-Patent Literature 3] Cancer Chemother. Pharmacol., 1993, vol. 32, p. 1-19

[Non-Patent Literature 4] Cell, 1989, vol. 58, p. 287-292

DISCLOSURE OF INVENTION

Problem to be Solved

The above compound (III) of the synthetic intermediate is prepared by Reaction A, in which the corresponding methoxycarbonyl compound (I') is converted to methoxymethylamide (VII), and followed by Reaction B with the compound (VII), wherein $R^2$, $R^3$ and $R^4$ are as defined above.

[Chemical Formula 3]
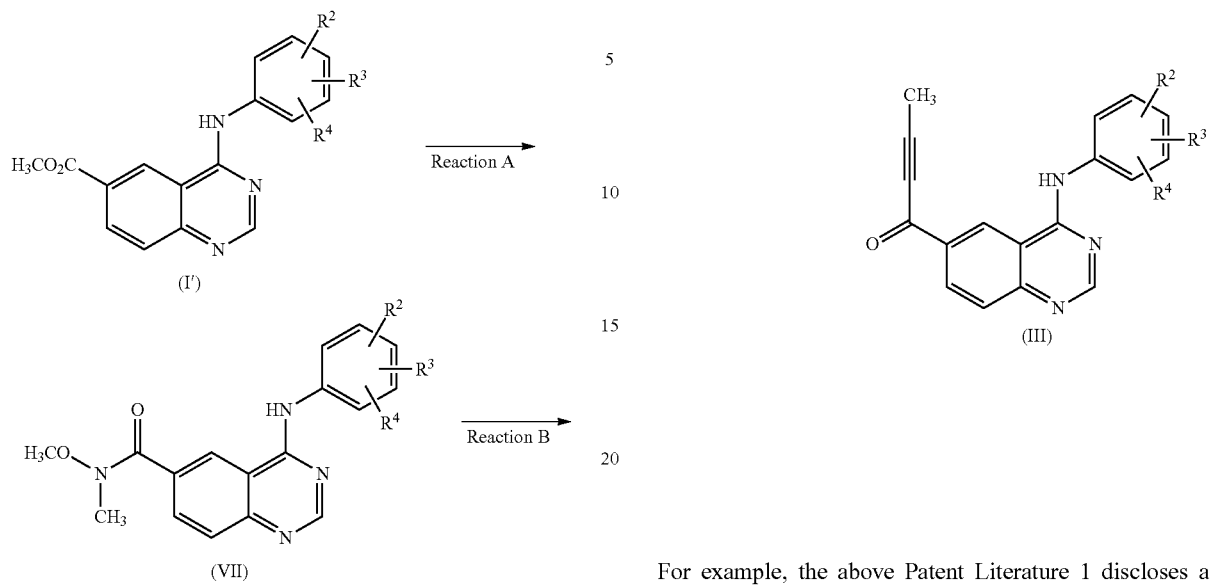
For example, the above Patent Literature 1 discloses a process for preparing the compound (VII-4):
[Chemical Formula 4]
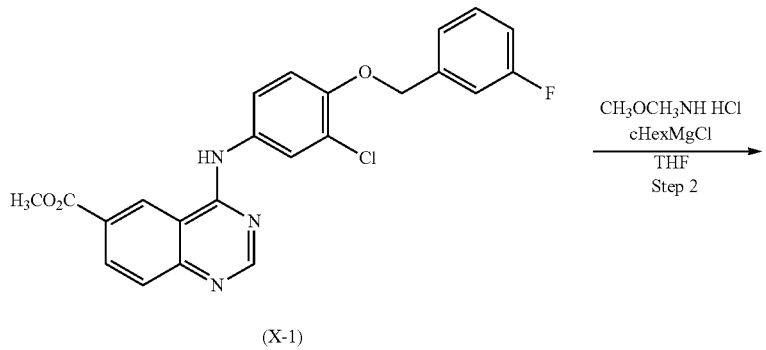
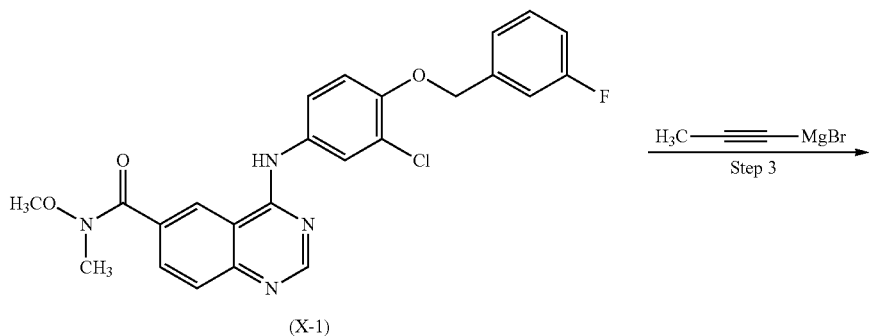

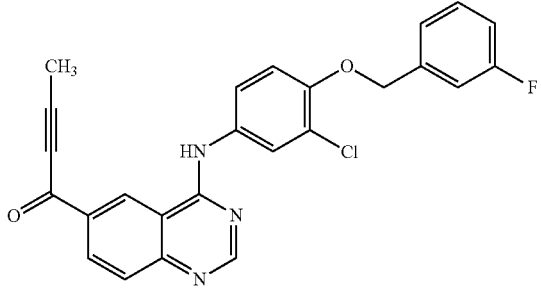

(VII-4)

in which a methoxy methyl amide (XI-1) is prepared from a methoxycarbonyl compound (X-1) (Step 2), and then reacted with Grignard reagent (Step 3).

However, the product yield was not sufficient and there was a need for improving the handleability.

Specifically, a process for preparing the compound represented by the formula (XI-1) from the compound represented by the formula (X-1) is disclosed in Reference Example 1 of Patent Literature 1. In the step, 3 equivalent of N,O-dimethyl hydroxylamine hydrochloride and 6 equivalent of iPrMgCl were used and it is shown that the reaction proceeded quantitatively.

Secondly, a process for preparing a compound represented by the formula (VII-4) from the compound represented by the formula (XI-1) is disclosed. It is shown that 3 equivalent of Grignard reagent is generated in the system of the reaction, and the reaction proceeds in about 79% yield.

Accordingly, the Patent Literature 1 describes that the compound represented by the formula (VII-4) is prepared in total yield of about 79% in two steps from the compound represented by the formula (X-1).

Means for Solving Problem

The inventors intensively studied and found that a compound (IV) is prepared from a methoxycarbonyl compound (I-1) in high yield by continuously conducting two reactions substantially as one step without isolating a compound (VII).

Further they confirmed that the continuous preparation method of a compound (III) can be applied to a wide range of a substrate (I) and the present invention was completed.

The present invention relates to:

(1) A process for preparing a compound represented by the formula (III):

[Chemical Formula 5]

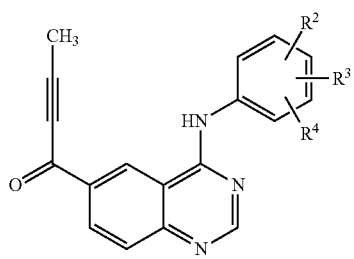

(III)

wherein $R^2$ is a hydrogen atom, halogen, substituted or unsubstituted alkyloxy, substituted or unsubstituted alkenyloxy, substituted or unsubstituted alkynyloxy or a group represented by the formula: —Y—$R^y$ wherein —Y— is —O—, —S—, —$SO_2$— or alkylene which may be intervened with —O—, —S— or —N($R^z$)—; and $R^y$ is substituted or unsubstituted aryl or substituted or unsubstituted heteroaryl; $R^z$ is a hydrogen atom, substituted or unsubstituted alkyl, substituted or unsubstituted acyl, substituted or unsubstituted alkyloxycarbonyl, substituted or unsubstituted alkenyloxycarbonyl, or substituted or unsubstituted aralkyloxycarbonyl;

$R^3$ and $R^4$ are each independently hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino;

a salt, or a solvate thereof;

characterized in that

Reaction A, in which a compound represented by the formula (I):

[Chemical Formula 6]

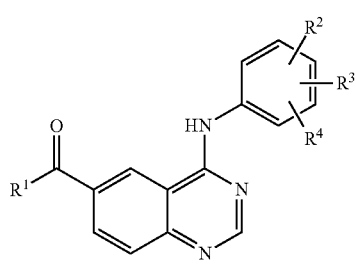

(I)

wherein $R^1$ is a group represented by the formula: —O—$R^x$ or —S—$R^x$ wherein $R^x$ is substituted or unsubstituted alkyl, substituted or unsubstituted alkenyl, substituted or unsubstituted alkynyl, substituted or unsubstituted aryl or a group of the formula (II):

[Chemical Formula 7]

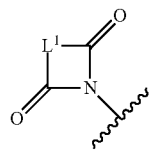
(II)

wherein L¹ is substituted or unsubstituted C2-C3 alkylene;
R², R³ and R⁴ are as defined above, is reacted with a compound represented by the formula: $(R^bO—)N(—R^a)H$ wherein $R^a$ and $R^b$ are each independently substituted or unsubstituted C1-C3 alkyl; or a salt thereof, and one or more metallic reagent(s) selected from the group consisting of Grignard reagent, sodium hydride, alkyllithium, alkenyllithium, alkynyllithium, phenyllithium, and lithium amide;

and Reaction B, in which the product of Reaction A is reacted with 1-propynyl metal acetylide;

are carried out substantially as one step by continuously conducting these two reactions;

(1') A process for preparing a compound represented by the formula (III):

[Chemical Formula 8]

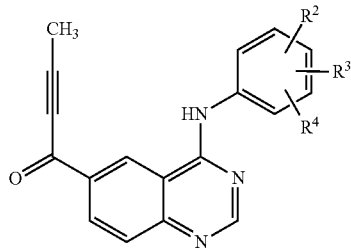
(III)

wherein R² is a hydrogen atom, halogen, substituted or unsubstituted alkyloxy, substituted or unsubstituted alkenyloxy, substituted or unsubstituted alkynyloxy or a group of the formula: —Y—R^y wherein —Y— is —O—, —S—, —SO₂— or alkylene which may be intervened with —O—, —S— or —N(R^z)—; and R^y is substituted or unsubstituted aryl or substituted or unsubstituted heteroaryl; R^z is a hydrogen atom, substituted or unsubstituted alkyl, substituted or unsubstituted acyl, substituted or unsubstituted alkyloxycarbonyl, substituted or unsubstituted alkenyloxycarbonyl, or substituted or unsubstituted aralkyloxycarbonyl;

R³ and R⁴ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino;

characterized in that

Reaction A, in which a compound represented by the formula (I):

[Chemical Formula 9]

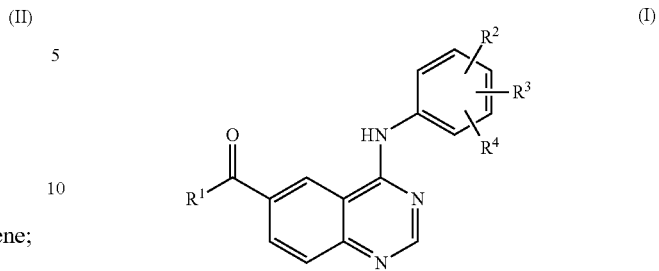
(I)

wherein R¹ is a group represented by the formula: —O—R^x or —S—R^x wherein R^x is substituted or unsubstituted alkyl, substituted or unsubstituted alkenyl, substituted or unsubstituted alkynyl, substituted or unsubstituted aryl or a group of the formula (II):

[Chemical Formula 10]

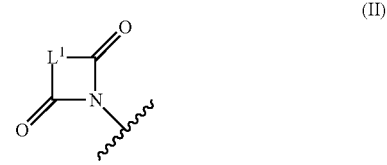
(II)

wherein L¹ is substituted or unsubstituted C2-C3 alkylene;
R², R³ and R⁴ are as defined above, is reacted with a compound represented by the formula: $(R^bO—)N(—R^a)H$ wherein $R^a$ and $R^b$ are each independently substituted or unsubstituted C1-C3 alkyl, or a salt thereof, and one or more metallic reagent(s) selected from the group consisting of Grignard reagent, sodium hydride, alkyllithium, alkenyllithium, alkynyllithium, phenyllithium, and lithium amide;

and Reaction B, in which the product of Reaction A is reacted with 1-propynyl metal acetylide;

are carried out substantially as one step by continuously conducting these two reactions;

(2) The process as described in above (1);

wherein R² is a group represented by the formula: —Y—R^y wherein —Y— is alkylene which may be intervened with —O—; and R^y is phenyl unsubstituted or substituted with a substituent selected from a substituent group p consisting of [halogen, carboxy, alkyl, haloalkyl, hydroxyalkyl, alkyloxy, alkyloxycarbonyl and substituted or unsubstituted amino], pyridyl unsubstituted or substituted with a substituent selected from a substituent group p, furyl unsubstituted or substituted with a substituent selected from a substituent group p, thienyl unsubstituted or substituted with a substituent selected from a substituent group p, thiazolyl unsubstituted or substituted with a substituent selected from a substituent group p, or oxazolyl unsubstituted or substituted with a substituent selected from a substituent group p;

R³ is substituted or unsubstituted alkynyl, substituted or unsubstituted alkyloxy or halogen; and R⁴ is a hydrogen atom;

(3) The process as described in above (1) or (2) or (1'), wherein the compound represented by the formula (III) is a crystalline form;

(3') The process as described in above (1) or (2), wherein the compound represented by the formula (III), a salt or a solvate thereof is a crystalline form;

(4) The process as described in any one of above (1) to (3), (1') or (3'), wherein the compound represented by the formula (III) is a compound represented by the formula (IV):

[Chemical Formula 11]

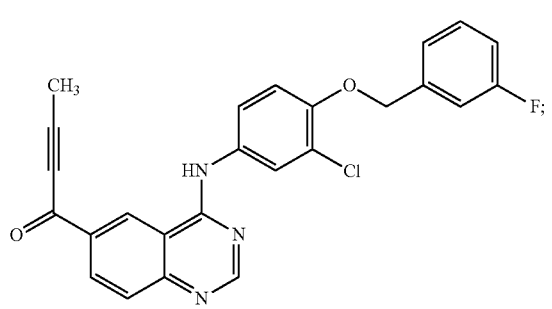

(IV)

(4') The process as described in any one of above (1) to (3), wherein the compound represented by the formula (III) is a compound represented by the formula (IV):

[Chemical Formula 12]

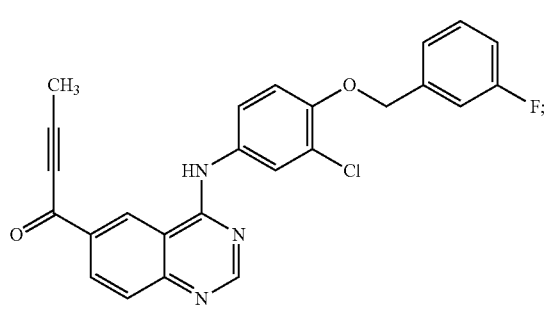

(IV)

(5) The process as described in above (4), comprising a step wherein the compound represented by the formula (IV) is recrystallized from an organic solvent;

(6) A process for preparing a compound represented by the formula (VI):

[Chemical Formula 13]

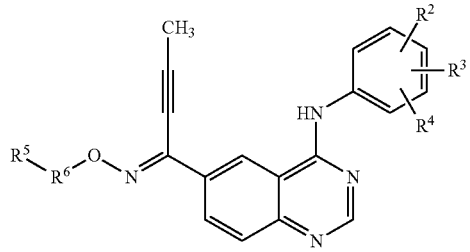

(VI)

wherein $R^2$, $R^3$ and $R^4$ are as defined in above (1) and $R^5$ is substituted or unsubstituted aryl, substituted or unsubstituted heteroaryl, substituted or unsubstituted heterocyclyl or substituted or unsubstituted amino, and $R^6$ is substituted or unsubstituted C1-3 alkylene, characterized in that the compound represented by the formula (III), which was prepared by the process as described in any one of above (1) to (3), (1') or (3'), is reacted with a compound represented by the formula (V): $R^5$—$R^6$—O—$NH_2$ wherein $R^5$ and $R^6$ are as defined above;

(6') A process for preparing the compound represented by the formula (VI):

[Chemical Formula 14]

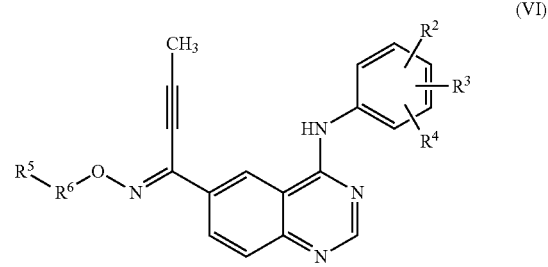

(VI)

wherein $R^2$, $R^3$ and $R^4$ are as defined in above (1) and $R^5$ is substituted or unsubstituted aryl, substituted or unsubstituted heteroaryl, substituted or unsubstituted heterocyclyl or substituted or unsubstituted amino, and $R^6$ is substituted or unsubstituted C1-3 alkylene, a salt or a solvate thereof;

characterized in that the compound represented by the formula (III), a salt or a solvate thereof, which was prepared by the process as described in any one of above (1) to (3), is reacted with a compound represented by the formula (V): $R^5$—$R^6$—O—$NH_2$ wherein $R^5$ and $R^6$ are as defined above;

(7) A process for preparing a compound represented by the formula (VI'):

[Chemical Formula 15]

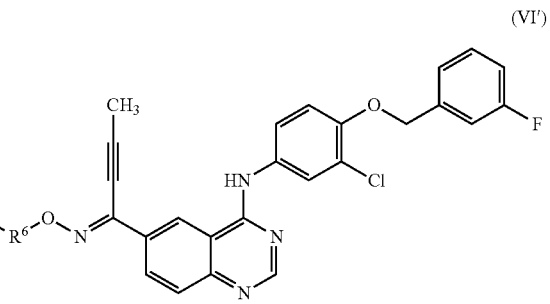

(VI')

wherein $R^5$ and $R^6$ are as defined in above (5), a salt or a solvate thereof, characterized in that the compound represented by the formula (IV), which was prepared by the process as described in above (4), is reacted with the compound represented by the formula (V): $R^5$—$R^6$—O—$NH_2$ wherein $R^5$ and $R^6$ are as defined above;

(7') A process for preparing a compound represented by the formula (VI'):

[Chemical Formula 16]

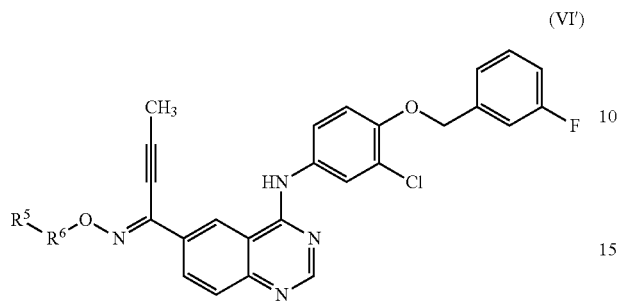

(VI')

wherein $R^5$ and $R^6$ are as defined in above (5), characterized in that
the compound represented by the formula (IV), a salt or a solvate thereof, which was prepared by the process as described in above (4) or (5),
is reacted with the compound represented by the formula (V): $R^5$—$R^6$—O—$NH_2$ wherein $R^5$ and $R^6$ are as defined above;

(8) A crystalline form of monohydrate of the compound represented by the formula (IV):

[Chemical Formula 17]

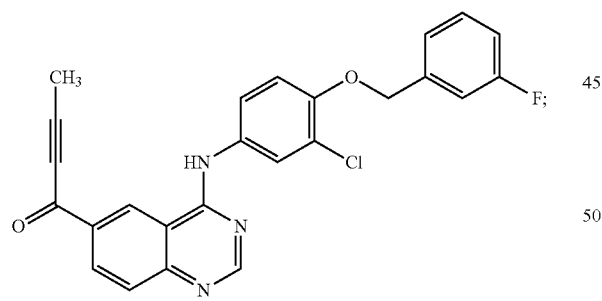

(IV)

(9) The crystalline form as described in above (8) wherein diffraction angle 2θ of major peaks of the powder X-Ray diffraction analysis are 5.6°±0.2°, 7.6°±0.2°, 11.6°±0.2°, 19.1°±0.2°, 25.0°±0.2° and 25.7°±0.2°;
(10) The crystalline form represented by the formula of (IV) as described in above (8) wherein diffraction angle 2θ of major peaks of the powder X-Ray diffraction analysis are 5.6°±0.1°, 7.6°±0.1°, 11.6°±0.1°, 19.1°±0.1°, 25.0°±0.1° and 25.7°±0.1°;
(11) The crystalline form described in above (8) wherein the crystalline form is characterized by powder X-Ray diffraction analysis spectrum substantially corresponding to FIG. 1;

(12) A crystalline form of the compound represented by the formula (IV):

[Chemical Formula 18]

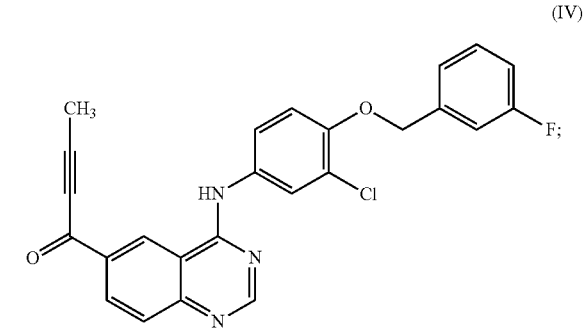

(IV)

(13) The crystalline form of the compound represented by the formula (IV) wherein diffraction angle 2θ of main peaks of the powder X-Ray diffraction analysis are 12.2°±0.2°, 13.5°±0.2°, 13.8°±0.2°, 18.4°±0.2°, 18.7°±0.2°, 20.2°±0.2°, 21.8°±0.2°, 22.0°±0.2°, 29.3°±0.2° and 29.7°±0.2°; and
(14) The crystalline form of the compound represented by the formula (IV) wherein diffraction angle 2θ of major peaks of the powder X-Ray diffraction analysis are 12.2°±0.1°, 13.5°±0.1°, 13.8°±0.1°, 18.4°±0.1°, 18.7°±0.1°, 20.2°±0.1°, 21.8°±0.1°, 22.0°±0.1°, 29.3°±0.1° and 29.7°±0.1°.

EFFECT OF INVENTION

A compound (III) which is useful as a synthetic intermediate is prepared from the corresponding methoxy carbonyl compound in high yield. Also as the method enables the reduction in amount of the base and the reagent as compared to the conventional method, it is an excellent method for industrial application.

BRIEF DESCRIPTION OF DRAWINGS

FIG. 1 shows data of powder X-Ray diffraction measurement of the crystalline form of the compound (IV) monohydrate (Example 1-1).

BEST MODE FOR CARRYING OUT THE INVENTION

The continuous preparation process comprises Reaction A, in which a compound represented by the following formula (I):

[Chemical Formula 19]

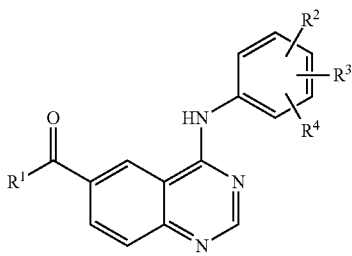

(I)

wherein R$^1$ is a group of the formula: —O—R$^x$ or —S—R$^x$ wherein R$^x$ is substituted or unsubstituted alkyl, substituted or unsubstituted alkenyl, substituted or unsubstituted alkynyl, substituted or unsubstituted aryl or a group of the formula (II):

[Chemical Formula 20]

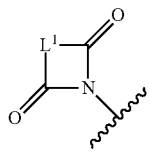

(II)

wherein L$^1$ is substituted or unsubstituted C2-C3 alkylene; R$^2$ is hydrogen atom, halogen, substituted or unsubstituted alkyloxy, substituted or unsubstituted alkenyloxy, substituted or unsubstituted alkynyloxy and a group of the formula: —Y—R$^y$, wherein —Y— is —O—, —S—, —SO$_2$— or alkylene which may be intervened with —O—, —S— or —N(R$^z$)—; R$^y$ is substituted or unsubstituted aryl or substituted or unsubstituted heteroaryl; and R$^z$ is hydrogen atom, substituted or unsubstituted alkyl, substituted or unsubstituted acyl, substituted or unsubstituted alkyloxycarbonyl, substituted or unsubstituted alkenyloxycarbonyl and substituted or unsubstituted aralkyloxycarbonyl;

R$^3$ and R$^4$ are each independently hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano and substituted or unsubstituted amino;

is reacted with a compound represented by the formula: (R$^b$O—)N(—R$^a$)H wherein R$^a$ and R$^b$ are each independently substituted or unsubstituted C1-C3 alkyl: or a salt thereof, and one or more metallic reagent(s) selected from the group consisting of Grignard reagent, sodium hydride, alkyllithium, alkenyllithium, alkynyllithium, phenyllithium, and lithium amide;

as a first step.

Examples of a solvent which is used in the first step is not limited as far as it does not inhibit the reaction include ethers such as tetrahydrofuran (THF), cyclopentyl methyl ether (CPME), diethyl ether, methyl tert-butyl ether and the like, hydrocarbons such as toluene, heptane, cyclohexane and the like or halogenated solvents such as methylene chloride and the like. For example, THF is used as a solvent. A mixture thereof can also be used.

The reaction temperature is usually in the range from −70° C. to 80° C., for example from −20° C. to 20° C.

The reaction is usually conducted by dissolving or suspending the compound (I) and the compound represented by the formula: (R$^b$O—)N(—R$^a$)H wherein R$^a$ and R$^b$ are as defined above or a salt thereof in the solvent described above and adding the metallic reagent dropwise thereto. The amount of the compound represented by the formula: (R$^b$O—)N(—R$^a$)H wherein R$^a$ and R$^b$ are as defined above or a salt thereof used is usually 1-4 equivalent, for example 1.0 to 1.5 equivalent.

Examples of the metallic reagent include Grignard reagent, sodium hydride, alkyllithium, alkenyllithium, alkynyllithium, phenyllithium, and lithium amide.

Examples of Grignard reagent include cyclohexyl magnesium chloride, cyclohexyl magnesium bromide, isopropyl magnesium chloride, isopropyl magnesium bromide and the like.

Examples of alkyllithium include methyllithium, n-buthyllithium, sec-buthyllithium, tert-buthyllithium and the like.

Examples of alkenyllithium include vinyllithium and the like.

Examples of alkynyllithium include ethynyllithium and the like.

Although the above metallic reagents are commercially available, compounds derived from known compounds using conventional method can also be used. Also 1-propynyl metal acetylide which is used in Reaction B can be used as the metallic reagent. As used herein, metal acetylide is a metal reagent prepared by displacing a hydrogen atom of acetylene or alkyl-substituted acetylene with a metal. 1-propynyl metal acetylide is a metal reagent prepared by displacing a hydrogen atom of 1-propyne with a metal. The amount of the metallic reagent used is usually 3-9 equivalent, for example 3-4 equivalent.

Further, when the compound represented by the formula: (R$^b$O—)N(—R$^a$)H wherein R$^a$ and R$^b$ are as defined above is free of salt, the amount of the metallic reagent used is 2-3 equivalent for example.

In the continuous preparation process of the present invention, Reaction A is continuously followed by Reaction B. Specifically, after adding the above metallic reagent dropwise, the reaction temperature is set in the range from −50° C. to 80° C., for example from 30° C. to 70° C. and 1-propynyl metal acetylide is added thereto.

After adding the above metallic reagent dropwise, the reaction mixture may be stirred for 0.5 to 1 hr, the temperature is adjusted and then 1-propynyl metal acetylide can be added thereto. Alternatively, the temperature of the mixture is adjusted right after adding the above metallic reagent and then 1-propynyl metal acetylide can be added thereto.

After adding 1-propynyl metal acetylide, the mixture is stirred until the reaction is completed, for example for about 0.5 to 48 hr.

Examples of the metals of the said metal acetylide include Li, MgX, Cu, Zn, Na, K and the like and MgX can be used for example. The said reagent is easily available as Grignard reagent of propylene. Alternatively, 1-propynyl metal acetylide generated in the reaction system can be used as described in Patent Literature 1. As for X, Br, Cl, and I are included. For example, Cl, Br can be used.

The amount of the said metal acetylide used is usually 1 to 4 equivalent and 1 to 2 equivalent for example.

According to the continuous preparation process of the present invention, the compound represented by the formula (III), a salt or a solvate thereof is prepared from the compound represented by the formula (I) substantially as one step.

Herein "continuously carried out" means to conduct a next step (Step B) without isolating the product of the above Reaction A.

The compound of the formula (VI):

[Chemical formula 21]

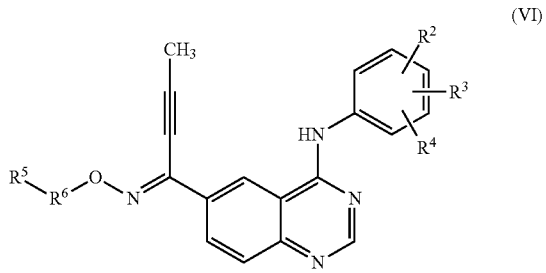

(VI)

wherein $R^2$, $R^3$ and $R^4$ are as defined above, $R^5$ is substituted or unsubstituted aryl, substituted or unsubstituted heteroaryl, substituted or unsubstituted heterocyclyl, or substituted or unsubstituted amino, and $R^6$ is substituted or unsubstituted C1-3 alkylene, a salt or a solvate thereof which is useful as a dual inhibitor of tyrosine kinase is prepared from the formula (III):

[Chemical formula 22]

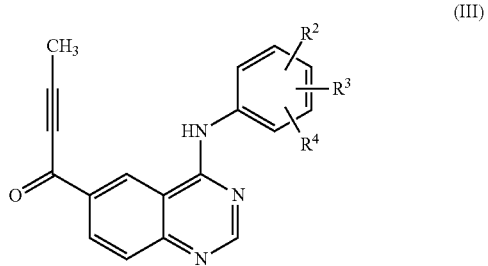

(III)

wherein $R^2$, $R^3$ and $R^4$ are as defined above, a salt or a solvate thereof, which was prepared by the continuous preparation process of the present invention, is reacted with the compound of the formula (V): $R^5-R^6-O-NH_2$ wherein $R^5$ and $R^6$ are as defined above, or a salt thereof.

Also among the compounds of the formula (III), the compound of the formula (IV):

[Chemical formula 23]

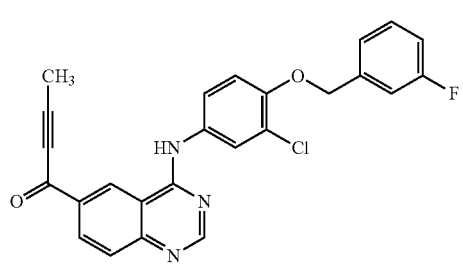

(IV)

can be crystallized from a water-tetrahydrofuran (THF)-methanol mixture. The solvent used for the crystallization is not limited, but ethyl acetate, tetrahydrofuran (THF), alcohol, water or the mixture thereof can be used.

The said crystalline form is excellent in handleability when performing the above steps or preparing a pharmaceutical composition comprising the compound represented by the formula (VI) or (VI') as an active ingredient, also useful for preparing a pharmaceutical composition because of high purity.

Also X-Ray diffraction pattern can be obtained from powder X-Ray diffraction analysis of the crystalline form. X-Ray diffraction pattern for the crystalline form of the compound represented by the formula (IV) is shown in Example 1 below [conditions for measuring X-Ray diffraction: RINT X-Ray Diffractometer (TTR III), CuKα X-ray Tubes, tube voltage: 50 Kv, tube current: 300 mA, d sin θ=nλ, wherein n is an integer, d: lattice spacing (Å), θ: diffraction angle (°, degree), λ: 1.5418 Å]. This crystalline form is characterized by each diffraction angle or a value of lattice spacing.

As used herein, "halogen" means fluorine, chlorine, bromine, and iodine. Examples include fluorine, chorine, and bromine.

As used herein, "alkyl" which is used alone or in combination with other term includes a straight or branched monovalent hydrocarbon group having 1 to 10 carbon atom(s). Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, n-nonanyl, n-decanyl and the like. Examples include C1-C10 alkyl. Examples include C1-C6 alkyl. Examples include C1-C4 alkyl.

As used herein, examples of "alkyloxy" include methyloxy, ethyloxy, n-propyloxy, isopropyloxy, n-butyloxy, isobutyloxy, sec-butyloxy, tert-butyloxy, n-pentyloxy, n-hexyloxy, n-heptyloxy, n-octyloxy, n-nonanyloxy, n-decanyloxy and the like. Examples include C1-C6 alkyloxy. Examples include C1-C3 alkyloxy.

As used herein, examples of "alkyloxycarbonyl" include methyloxycarbonyl, ethyloxycarbonyl, n-propyloxycarbonyl, isopropyloxycarbonyl, n-butyloxycarbonyl, t-butyloxycarbonyl, n-pentyloxycarbonyl and the like. Examples include C1-C6 alkyloxycarbonyl. Examples include C1-C3 alkyloxycarbonyl.

As used herein, "alkenyl" includes a straight or branched monovalent hydrocarbon group having 2 to 8 carbon atom(s) and 1 or 2 or more double bond(s). The alkenyl may have a triple bond in a chain. Examples include vinyl, allyl, 1-propenyl, 2-propenyl, various butenyl isomers and the like. Examples include C2-C6 alkenyl. Examples include C2-C4 alkenyl.

As used herein, examples of "alkenyloxy" include vinyloxy, allyloxy, 1-propenyloxy, 2-propenyloxy, various butenyloxys and the like. Examples include C2-C6 alkenyloxy. Examples include C2-C4 alkenyloxy.

As used herein, examples of "alkenyloxycarbonyl" include vinyloxycarbonyl, allyloxycarbonyl, 1-propenyloxycarbonyl, 2-propenyloxycarbonyl, various butenyloxycarbonyls and the like. Examples include C2-C6 alkenyloxycarbonyl. Examples include C2-C4 alkenyloxycarbonyl.

As used herein, "alkynyl" includes a straight or branched monovalent hydrocarbon group having 2 to 8 carbon atom(s) and having 1 or 2 or more triple bond(s). Examples include ethynyl, 1-propynyl, 2-propynyl, 1-butynyl, 2-butynyl, 3-butynyl, 1-pentynyl, 2-pentynyl, various pentynyl isomers and the like. Examples include C2-C6 alkynyl. Examples include C2-C4 alkynyl.

As used herein, examples of "alkynyloxy" include ethynyloxy, propynyloxy, butynyloxy, pentynyloxy and the like. Examples include C2-C6 alkynyloxy. Examples include C2-C4 alkynyloxy.

As used herein, "alkylene" which is used alone or in combination with other term includes a straight or branched divalent hydrocarbon group having 1 to 4 carbon atom(s). Examples include methylene, ethylene, propylene, butylene and the like. Examples include C1-C3 alkylene. Examples include C1-C2 alkylene.

As used herein, "aryl" which is used alone or in combination with other term includes a monocyclic or fused cyclic aromatic hydrocarbon. Examples include phenyl, 1-naphthyl, 2-naphthyl, anthryl and the like. Examples include phenyl, 1-naphthyl, and 2-naphthyl. An example includes phenyl.

As used herein, "aralkyl" includes the above "alkyl" substituted with one or two or more of the above "aryl", and these can be substituted at all possible positions. Examples include benzyl, phenylethyl (e.g. 2-phenylethyl, and the like), phenylpropyl (e.g. 3-phenylpropyl, and the like), naphthylmethyl (e.g. 1-naphthylmethyl, 2-naphthylmethyl, and the like), anthrylmethyl (e.g. 9-anthrylmethyl, and the like) and the like. Examples include benzyl and phenylethyl.

As used herein, examples of "aralkyloxy" include benzyloxy, phenylethyloxy (e.g. 2-phenylethyloxy, and the like), phenylpropyloxy (e.g. 3-phenylpropyloxy, and the like), naphthylmethyloxy (e.g. 1-naphthylmethyloxy, 2-naphthylmethyloxy, and the like), anthrylmethyloxy (e.g. 9-anthrylmethyloxy, and the like) and the like. Examples include benzyloxy, and phenylethyloxy.

As used herein, examples of "aralkyloxycarbonyl" include benzyloxycarbonyl, phenylethyloxycarbonyl (e.g. 2-phenylethyloxycarbonyl, and the like), phenylpropyloxycarbonyl (e.g. 3-phenylpropyloxycarbony, and the like), naphthylmethyloxycarbonyl (e.g. 1-naphthylmethyloxycarbonyl, 2-naphthylmethyloxycarbonyl, and the like), anthrylmethyloxycarbonyl (e.g. 9-anthrylmethyloxycarbonyl, and the like) and the like.
Examples include benzyloxycarbonyl and phenylethyloxycarbonyl.

As used herein, "heteroaryl" which is used alone, or in combination with other term includes a 5- to 6-membered aromatic ring group containing one or more of arbitrarily selected oxygen atom, sulfur atom or nitrogen atom in a ring. This may be fused with the "aryl" or other heteroaryl at all possible positions. When heteroaryl is any of a monocycle and a fused cycle, it can bind at all possible positions. Examples include pyrrolyl (e.g. 1-pyrrolyl, 2-pyrrolyl, 3-pyrrolyl), furyl (e.g. 2-furyl, 3-furyl), thienyl (e.g. 2-thienyl, 3-thienyl), imidazolyl (e.g. 2-imidazolyl, 4-imidazolyl), pyrazolyl (e.g. 1-pyrazolyl, 3-pyrazolyl), isothiazolyl (e.g. 3-isothiazolyl), isooxazolyl (e.g. 3-isooxazolyl), oxazolyl (e.g. 2-oxazolyl), thiazolyl (e.g. 2-thiazolyl, 5-thiazolyl), pyridyl (e.g. 2-pyridyl, 3-pyridyl, 4-pyridyl), pyrazinyl (e.g. 2-pyrazinyl), pyrimidinyl (e.g. 2-pyrimidinyl, 4-pyrimidinyl), pyridazinyl (e.g. 3-pyridazinyl), triazolyl, tetrazolyl (e.g. 1H-tetrazolyl), oxadiazolyl (e.g. 1,3,4-oxadiazolyl), thiadiazolyl (e.g. 1,3,4-thiadiazolyl), indolydinyl (e.g. 2-indolydinyl, 6-indolydinyl), isoindolyl (e.g. 2-isoindolyl), indolyl (e.g. 1-indolyl, 2-indolyl, 3-indolyl), indazolyl (e.g. 3-indazolyl), purinyl (e.g. 8-purinyl), quinolizinyl (e.g. 2-quinolizinyl), isoquinolyl (e.g. 3-isoquinolyl), quinolyl (e.g. 2-quinolyl, 5-quinolyl), phthalazinyl (e.g. 1-phthalazinyl), naphthyridinyl (e.g. 2-naphthyridinyl), quinazolinyl (e.g. 2-quinazolinyl), cinnolinyl (e.g. 3-cinnolinyl), pteridinyl (e.g. 2-pteridinyl), carbazolyl (e.g. 2-carbazolyl, 4-carbazolyl), phenanthridinyl (e.g. 2-phenanthridinyl, 3-phenanthridinyl), acridinyl (e.g. 1-acridinyl, 2-acridinyl), dibenzofuranyl (e.g. 1-dibenzofuranyl, 2-dibenzofuranyl), benzoimidazolyl (e.g. 2-benzoimidazolyl), benzoisooxazolyl (e.g. 3-benzoisooxazolyl), benzooxazolyl (e.g. 2-benzooxazolyl), benzooxadiazolyl (e.g. 4-benzooxadiazolyl), benzoisothiazolyl (e.g. 3-benzoisothiazolyl), benzothiazolyl (e.g. 2-benzothiazolyl), benzofuryl (e.g. 3-benzofuryl), benzothienyl (e.g. 2-benzothienyl), 4,5-dihydronaphtho[1,2-d]thiazolyl, 4H-chromeno[4,3-d]thiazolyl, 4H-thiochromeno[4,3-d]thiazolyl, 4,5-dihydrothiazolo[5,4-c]quinolyl, 8H-indeno[1,2-d]thiazolyl, 5,6-dihydro-4H-3-thia-1-azabenzo[e]azulenyl and the like.

As used herein, the term "heterocyclyl group" which is used alone, or in combination with other term includes a non-aromatic 5- to 7-membered ring containing one or more arbitrary selected from an oxygen atom, a sulfur atom and a nitrogen atom in a ring, and a group derived from a ring in which other one or more "heterocyclyl" or "heteroaryls" is fused thereto. Examples include pyrrolidinyl (e.g. 1-pyrrolidinyl, 2-pyrolidinyl), pyrrolinyl (e.g. 3-pyrrolinyl), imidazolidinyl (e.g. 2-imidazolidinyl), imidazolinyl (e.g. imidazolinyl), pyrazolidinyl (e.g. 1-pyrazolidinyl, 2-pyrazolidinyl), pyrazolinyl (e.g. pyrazolinyl), piperidyl (e.g. piperidino, 2-piperidyl), piperazinyl (e.g. 1-piperazinyl, 2-piperazinyl), indolinyl (e.g. 1-indolinyl), isoindolinyl (e.g. isoindolinyl), morpholinyl (e.g. morpholino, 2-morpholinyl, 3-morpholinyl), tetrahydrofuranyl, dihydropyranyl, tetrahydropyranyl, dioxolanyl, tetrahydrothienyl, dihydrothiopyranyl, tetrahydrothiofuranyl, decahydroisoquinolinyl, azepinyl, oxepinyl, dihydrooxepinyl, tetrahydrooxepinyl, oxepanyl, 4,5,6,7-tetrahydrothieno[3,2]pyridyl, 2-oxa-5-aza-bicyclo[2.2.1]hepta-5-yl, hexahydropyrazyl[2.1-b][1,3]oxadin-8-yl and the like.

As used herein, examples of heterocyclyl of $R^5$ are morpholinyl, azetidinyl, pyrrolidinyl, and piperazinyl.

As used herein, the above "alkyl" which is substituted with the above "halogen" at 1 to 8 positions, or 1 to 5 positions for example is included. Examples include trifluoromethyl, trichloromethyl, difluoroethyl, trifluoroethyl, dichloroethyl, trichloroethyl and the like. Examples include C1-C6 alkyl which is substituted with above "halogen" at 1 to 5 positions.

As used herein, the term "cycloalkyl" which is used alone or in combination with other term includes C3-C8 cycloalkyl. Examples include cyclopropyl, cyclobutyl, cyclopentyl, cyclohexyl, cycloheptyl and cyclooctyl. Examples include C5-C6 cycloalkyl.

As used herein, the term "acyl" include formyl, alkylcarbonyl in which the alkyl part is the "alkyl", haloalkylcarbonyl in which the haloalkyl part is the "haloalkyl", alkenylcarbonyl in which the alkenyl part is the "alkenyl", aralkylcarbonyl in which the aralkyl part is the "aralkyl", arylcarbonyl in which the aryl part is the "aryl", heteroarylcarbonyl in which the heteroaryl part is the "heteroaryl", heterocyclylcarbonyl in which the heterocyclyl part is the "heterocyclyl" and cycloalkylcarbonyl in which the cycloalkyl part is the "cycloalkyl". Examples include acetyl, propionyl, butyroyl, trifluoromethylcarbonyl, vinylcarbonyl, phenylacetyl, benzoyl and the like. The "alkyl", the "alkenyl" the "aryl", the "heteroaryl", the "heterocyclyl" and the "cycloalkyl" may be substituted with each substituent described below.

A substituent in the "substituted alkyl", "substituted alkenyl", "substituted alkynyl", "substituted alkyloxy", "substituted alkyloxycarbonyl", "substituted alkenyloxy", "substituted alkenyloxycarbonyl", "substituted alkynyloxy", "substituted alkylene", "substituted aralkyloxy carbonyl", "substituted aryl", "substituted heteroaryl", "substituted heterocyclyl", "substituted acyl", "substituted cycloalkyl" and "substituted amino" is selected from the group consisting of hydroxy, carboxy, halogen, haloalkyl (e.g. $CF_3$, $CH_2CF_3$, $CH_2CCl_3$), alkyl (e.g. methyl, ethyl, isopropyl, tert-butyl), alkenyl (e.g. vinyl), alkynyl (e.g. ethynyl), cycloalkyl (e.g. cyclopropyl), cycloalkenyl (e.g. cyclopropenyl), alkyloxy (e.g. methoxy, ethoxy, propoxy, butoxy), haloalkyloxy (e.g. $OCF_3$), alkenyloxy (e.g. vinyloxy, allyloxy), aryloxy (e.g. phenoxy), alkoxycarbonyl (e.g. methoxycarbonyl, ethoxy-carbonyl, tert-butoxycarbonyl), nitro, nitroso, optionally substituted amino (e.g. alkylamino (e.g. methylamino, ethylamino, dimethylamino), acylamino (e.g. acetylamino, benzoylamino), aralkylamino (e.g. benzylamino, tritylamino), hydroxyamino, alkoxycarbonylamino, alkylsulfonylamino, carbamoylamino, heterocyclylcarbonylamino, arylsulphonylamino), azide, aryl (e.g. phenyl), aralkyl (e.g. benzyl), cyano, isocyano, isocyanato, thiocyanato, isothiocyanato, mercapto, alkylthio (e.g. methylthio), alkylsulfonyl (e.g. methanesulfonyl, ethanesulfonyl), alkylsulfonyloxy (e.g. methanesulfonyloxy, ethanesulfonyloxy), optionally substituted carbamoyl (e.g. alkylcarbamoyl (e.g. methylcarbamoyl, ethylcarbamoyl, dimethylcarbamoyl), alkylsulphonylcarbamoyl), sulfamoyl, acyl (e.g. formyl, acetyl), formyloxy, haloformyl, oxalo, thioformyl, thiocarboxy, dithiocarboxy, thiocarbamoyl, sulfino, sulfo, sulfonyl, sulfinyl, sulfoamino, hydrazino, azide, ureido, amidino, guanidino, phthalimide, oxo, cycloalkyl, cycloalkenyl, aryl, heteroaryl, heterocyclyl, alkylene, optionally substituted alkylendioxy (—O—CH$_2$—O—, —O—CH$_2$—CH$_2$—O—, —O—CH$_2$—CH$_2$—CH$_2$—O— and the like), heteroaryloxy, heterocyclyloxy, alkyloxycarbonyl, aryloxycarbonyl, heteroaryloxycarbonyl, heterocyclyloxycarbonyl, alkylcarbonyloxy, arylcarbonyloxy, heteroarylcarbonyloxy, heterocyclylcarbonyloxy, alkylcarbonyl, arylcarbonyl, heteroarylcarbonyl, heterocyclylcarbonyl, alkylthio, arylthio, heteroarylthio, heterocyclylthio, alkylsulfonyl, arylsulfonyl, heteroarylsulfonyl, heterocyclylsulfonyl, thiocarbamoyl", "sulfamoyl" and the like. These can be substituted with 1 to 4 substituent(s).

A substituent of the "substituted amino" in R$^5$ includes alkyl (including hydroxyalkyl and alkyloxyalkyl), cycloalkyl and the like.

A substituent of the "substituted heterocyclyl" in R$^5$ includes hydroxy and the like.

As used herein, alkyl in "hydroxyalkyl", "aryloxycarbonyl", "arylcarbonyloxy", "alkylcarbonyl", "alkylthio" and "alkylsulfonyl" is the alkyl as defined above.

As used herein, heteroaryl in "heteroaryloxycarbonyl", "heteroarylcarbonyloxy", "heteroarylcarbonyl", "heteroarylthio" and "heteroarylsulfonyl" is the heteroaryl as defined above.

As used herein, heterocyclyl in "heterocyclyloxycarbonyl", "heterocyclylcarbonyloxy", "heterocyclylcarbonyl", "heterocyclylthio" and "heterocyclylsulfonyl" is the heterocyclyl as defined above.

As used herein, "an organic solvent" includes alcohols, ethers, hydrocarbons, halogenated solvents, polar solvents and the like. Examples of alcohols include methanol, ethanol, 1-propanol, 2-propanol, 1-butanol, 2-butanol, 3-butanol and the like. Examples of ethers include tetrahydrofuran (THF), cyclopentyl methyl ether (CPME), diethyl ether, methyl tert-butyl ether and the like. Examples of hydrocarbons include toluene, heptane, cyclohexane and the like. Examples of halogenated solvent include methylene dichloride, chloroform and the like. Examples of polar solvents include dimethylformamide, dimethyl sulfoxide, NMP and the like. Examples of other solvents include ethyl acetate, acetone, acetonitrile and the like. The mixture thereof is also used. The above solvents do not always need dehydration and when necessary, it can be performed by distillation of the organic solvent or by using dehydrating agents. Examples of dehydrating agents include molecular sieves, and molecular sieves 3A, 4A, 5A, 13A and the like are preferred.

Herein, the compound of the general formula (I), (III), (IV) and (V) may be converted to its salt form. Examples include salts of alkali metals (lithium, sodium, potassium and the like), alkaline-earth metals (magnesium, calcium and the like), ammonium, organic bases and amino acid, or salts of inorganic acids (hydrochloric acid, hydrobromic acid, phosphoric acid, sulfuric acid and the like), and organic acids (acetic acid, citric acid, maleic acid, fumaric acid, benzenesulfonic acid, p-toluenesulfonic acid and the like). The compound is converted to its salt form by a conventional method.

Also said compound may form a solvate. A solvate herein includes, for example, a solvate with an organic solvent, a hydrate and the like. When a solvate is formed, the compound may be coordinated with an arbitrary number of organic solvent molecules. When a hydrate is formed, the compound may be coordinated with an arbitrary number of water molecules.

The continuous preparation process of the present invention is preferably carried out when R$^2$ is a group of the formula: —Y—R$^y$ wherein —Y— is alkylene which may be intervened with —O—; and R$^y$ is phenyl unsubstituted or substituted with a substituent selected from a group p consisting of [halogen, carboxy, alkyl, haloalkyl, hydroxyalkyl, alkyloxy, alkyloxycarbonyl and substituted or unsubstituted amino], pyridyl unsubstituted or substituted with a substituent selected from a group p, furyl unsubstituted or substituted with a substituent selected from a group p, thienyl unsubstituted or substituted with a substituent selected from a group p, thiazolyl unsubstituted or substituted with a substituent selected from a group p, and oxazolyl unsubstituted or substituted with a substituent selected from a group p;

R$^3$ is substituted or unsubstituted alkynyl, substituted or unsubstituted alkyloxy or halogen; and R$^4$ is hydrogen.

For example, the preparation method is shown in the following scheme:

[Chemical formula 24]

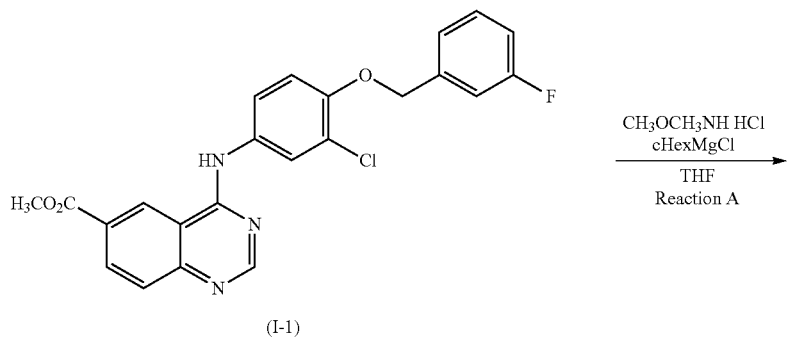

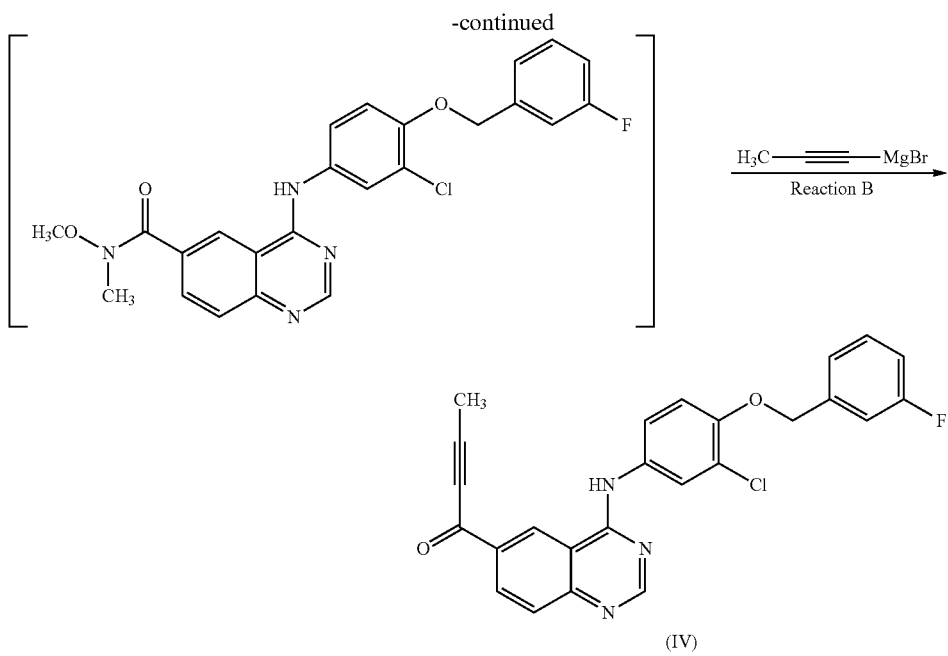
EXAMPLES
Example 1-1
Preparation of 4-(3-chloro-4-(3-fluorobenzyloxy)phenylamino)-6-(1-oxo-2-butyn-1-yl)quinazoline (IV)
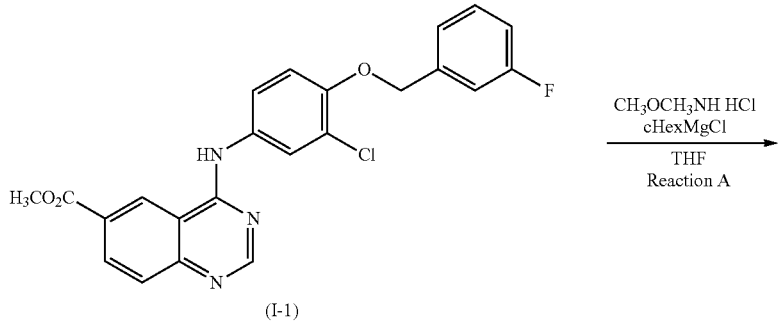
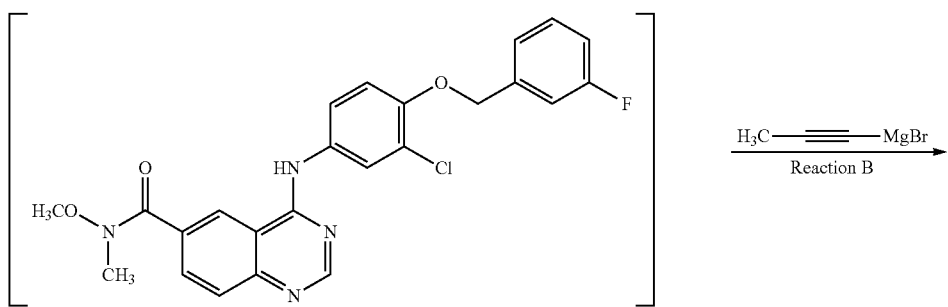

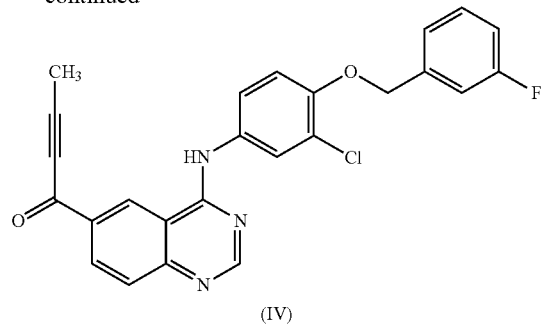

(IV)

A solution of a methoxy carbonyl derivative (I-1) (20.0 kg) and N,O-dimethylhydroxylamine hydrochloride (4.9 kg, 1.1 equiv) in tetrahydrofuran (100 L) was stirred and cooled to 0° C. After adding a solution of cyclohexyl magnesium chloride (20.9 kg, 3.2 equiv) in tetrahydrofuran dropwise, 1-propynyl magnesium bromide (9.8 kg, 1.5 equiv) in tetrahydrofuran was added at 55° C., stirred for about 3 hr and then cooled to room temperature. The reaction mixture was added dropwise to a solution of conc. hydrochloride (22.4 kg, 4.7 equiv) in methanol-water mixture previously cooled to 0° C., and then 200 L of water was added and stirred for 30 min at 5° C. The suspension was adjusted to pH 3.5 and filtered. The crystalline was washed with cooled aqueous tetrahydrofuran and methanol to give a compound (IV) (19.0 kg, 93% yield).

$^1$H-NMR (300 MHz, CDCl$_3$) δ 2.22 (s, 3H), 5.18 (s, 2H), 6.99-7.06 (m, 2H), 7.20-7.25 (m, 2H), 7.33-7.40 (m, 1H), 7.53 (dd, 1H, J=8.7, 2.5 Hz), 7.73 (s, 1H), 7.90 (d, 1H, J=2.6 Hz), 7.96 (d, 1H, J=8.6, 1.7 Hz), 8.52 (dd, 1H, J=8.6, 1.7 Hz), 8.73 (d, 1H, J=1.7 Hz), 8.79 (s, 1H).

Elemental analysis:
Calculated: C, 64.73; H, 4.13; N, 9.06; Cl, 7.64; F, 4.10
Found: C, 64.45; H, 4.10; N, 8.90; Cl, 7.65; F, 3.54. (1.0H$_2$O)

Example 1-2

A solution of a methoxy carbonyl derivative (I-1) (10.0 g) and N,O-dimethylhydroxylamine hydrochloride (2.45 g, 1.1 equiv) in tetrahydrofuran (50 mL) was stirred and cooled to 0° C. After adding a solution of cyclohexyl magnesium bromide (14.1 g, 3.3 equiv) in tetrahydrofuran dropwise, 1-propynyl magnesium bromide (4.9 g, 1.5 equiv) in tetrahydrofuran was added at 55° C., stirred for about 3 hr and then cooled to room temperature. The reaction mixture was added dropwise to a solution of conc. hydrochloride (11.9 g, 4.7 equiv) in methanol-water mixture previously cooled to 0° C., and then 100 mL of water was added and stirred for 30 min at 5° C. The suspension was adjusted to pH 3.5 and filtered. Filtered crystalline was dissolved in tetrahydrofuran-methanol mixture (330 mL). The solution was concentrated under reduced pressure, added methanol, cooled to 0° C. and filtered to give the compound (IV) (8.6 g, 85% yield).

Elemental analysis:
Calculated: C, 66.80; H, 3.90; N, 9.35; Cl, 7.89; F, 4.23.
Found: C, 66.80; H, 4.02; N, 9.34; Cl, 7.82; F, 4.02. (0.2H$_2$O)

Powder X-Ray Diffraction Measurement

Data of powder X-Ray diffraction measurement of the obtained crystalline form in each example is obtained according to powder X-Ray diffraction analysis method in General tests in Japanese Pharmacopoeia as following conditions:

Device:
RINT X-Ray Diffractometer (TTR III)
Method:
Samples are measured under following conditions:
Measuring method: Reflection method
Light source: Cu tube
Used Wavelength: CuKα ray
Tube current: 300 mA
Tube voltage: 50 Kv
Sampling plate: Aluminum Data of powder X-Ray diffraction measurements are shown in Table 1, 2 and FIG. 1. Table 1 and FIG. 1 show the data of the measurement of the compound of the formula (IV) in Example 1-1 and Table 2 shows the data of the measurement of the compound of the formula (IV) in Example 1-2.

TABLE 1

| peak no. | 2θ | set width of peak search | d value | intensity | relative intensity |
|---|---|---|---|---|---|
| 1 | 5.620 | 0.141 | 15.7123 | 4667 | 12 |
| 2 | 7.600 | 0.141 | 11.6227 | 6333 | 17 |
| 3 | 11.640 | 0.165 | 7.5962 | 29650 | 76 |
| 4 | 15.240 | 0.165 | 5.8090 | 7617 | 20 |
| 5 | 16.320 | 0.165 | 5.4269 | 5167 | 14 |
| 6 | 17.740 | 0.212 | 4.9956 | 11063 | 29 |
| 7 | 19.060 | 0.165 | 4.6525 | 4688 | 12 |
| 8 | 22.960 | 0.094 | 3.8703 | 3175 | 9 |
| 9 | 23.440 | 0.212 | 3.7921 | 8650 | 23 |
| 10 | 24.140 | 0.118 | 3.6837 | 5596 | 15 |
| 11 | 24.200 | 0.071 | 3.6747 | 4767 | 13 |
| 12 | 24.980 | 0.188 | 3.5617 | 12683 | 33 |
| 13 | 25.700 | 0.212 | 3.4635 | 39246 | 109 |
| 14 | 26.260 | 0.071 | 3.3909 | 4271 | 11 |
| 15 | 26.300 | 0.094 | 3.3858 | 4250 | 11 |
| 16 | 26.740 | 0.071 | 3.3311 | 3521 | 9 |
| 17 | 27.480 | 0.071 | 3.2431 | 3800 | 10 |
| 18 | 27.560 | 0.071 | 3.2338 | 4138 | 11 |
| 19 | 27.680 | 0.071 | 3.2201 | 4171 | 11 |
| 20 | 27.720 | 0.071 | 3.2155 | 4008 | 11 |
| 21 | 28.220 | 0.118 | 3.1597 | 5608 | 15 |
| 22 | 28.260 | 0.071 | 3.1553 | 5364 | 14 |
| 23 | 38.200 | 0.188 | 2.3540 | 31838 | 82 |

Diffraction angle of major peaks: 2θ=5.6±0.2°, 7.6±0.2°, 11.6±0.2°, 19.1±0.2°, 25.0±0.2° and 25.7±0.2°.

TABLE 2

| peak no. | 2θ | set width of peak search | d value | intensity | relative intensity |
|---|---|---|---|---|---|
| 1 | 8.100 | 0.141 | 10.9063 | 2319 | 1 |
| 2 | 12.160 | 0.165 | 7.2725 | 1161 | 1 |
| 3 | 16.200 | 0.188 | 5.4668 | 914 | 1 |
| 4 | 17.560 | 0.165 | 5.0464 | 831 | 1 |
| 5 | 18.340 | 0.141 | 4.8335 | 935 | 1 |
| 6 | 18.720 | 0.141 | 4.7362 | 2378 | 1 |
| 7 | 19.560 | 0.188 | 4.5347 | 619 | 1 |
| 8 | 20.200 | 0.118 | 4.3924 | 604 | 1 |
| 9 | 20.360 | 0.118 | 4.3582 | 783 | 1 |
| 10 | 21.840 | 0.141 | 4.0661 | 3466 | 1 |
| 11 | 22.020 | 0.118 | 4.0333 | 4020 | 1 |
| 12 | 22.700 | 0.118 | 3.9140 | 421 | 1 |
| 13 | 23.380 | 0.165 | 3.8017 | 594 | 1 |
| 14 | 23.700 | 0.235 | 3.7511 | 403 | 1 |
| 15 | 26.240 | 0.141 | 3.5256 | 1347 | 1 |
| 16 | 25.560 | 0.118 | 3.4822 | 787 | 1 |
| 17 | 26.340 | 0.118 | 3.3808 | 558 | 1 |
| 18 | 26.840 | 0.141 | 3.3189 | 6556 | 2 |
| 19 | 29.300 | 0.118 | 3.0456 | 1330 | 1 |
| 20 | 29.680 | 0.118 | 3.0075 | 701 | 1 |
| 21 | 34.500 | 0.141 | 2.5975 | 2388 | 1 |
| 22 | 36.660 | 0.141 | 2.4493 | 11166 | 3 |
| 23 | 36.900 | 0.188 | 2.4339 | 2326 | 1 |
| 24 | 38.320 | 0.141 | 2.3469 | 434987 | 100 |

Diffraction angle of major peaks: 2θ=12.2±0.2°, 13.5±0.2°, 13.8±0.2°, 18.4±0.2°, 18.7±0.2°, 20.2±0.2°, 21.8±0.2°, 22.0±0.2°, 29.3±0.2° and 29.7±0.2°.

Example 2

Preparation of 4-(3-chloro-4-(3-fluorobenzyloxy) phenylamino)-6-(1-((S)-morpholine-2-yl-methoxyimino)-2-butyn-1-yl)quinazoline.2HCl (VI-1)

[Chemical formula 26]

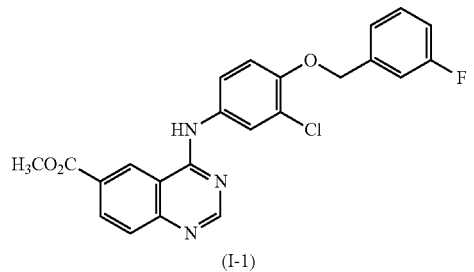

(I-1)

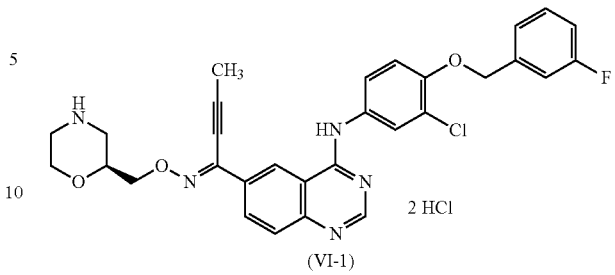

(VI-1)

(1) The compound (IV) was prepared according to the above Example 1.

(2) Preparation of 4-(3-chloro-4-(3-fluorobenzyloxy)phenylamino)-6-(1-((S)-morpholine-2-yl-methoxyimino)-2-butyn-1-yl)quinazoline.2HCl To a suspension of 4-(3-chloro-4-(3-fluorobenzyloxy)phenylamino)-6-(1-oxo-2-butyn-1-yl)quinazoline (IV) (786 mg) and tert-buthyl (S)-2-aminoxymethyl-morpholine-4-carboxylate (614 mg) in 1,4-dioxane (31 mL) was added 2 mol/L methanesulfonic acid aq. solution (2.21 mL) and stirred for 22 hr at 80° C. 2 mol/L methanesulfonic acid aq. solution (1.32 mL) was added and stirred for additional 5.5 hr. After the reaction was completed, the mixture was poured into ice-sodium hydrogen carbonate aq. solution and extracted with ethyl acetate. After the aqueous layer was extracted again with ethylacetate, all the organic layers were combined, washed with water and dried over anhydrous magnesium sulfate. The filtrate was concentrated and the residue was purified by silicagel column chromatography (eluted with chloroform:methanol=9:1) to give yellow oil. A solution of this oil in ethyl acetate (50 mL) was filtered and 4 mol/L hydrochloric acid-ethyl acetate (0.95 mL) was added under stirring and stirred for 1 hr at room temperature. The precipitate was filtered and washed with ethyl acetate and then hexane. The precipitate was recrystallized from methanol-ethyl acetate to give 4-(3-chloro-4-(3-fluorobenzyloxy)phenylamino)-6-(1-((S)-morpholine-2-yl-methoxyimino)-2-butyn-1-yl)quinazoline.2HCl (VI-1) (839 mg) as yellow crystalline.

$^1$H-NMR (d$_6$-DMSO, δ): 11.69 (1H, bs), 9.49-9.37 (2H, m), 9.05 (1H, s), 8.88 (1H, s), 8.38 (1H, dd, J=1.5 Hz, J=8.7 Hz), 7.96 (1H, d, J=8.7 Hz), 7.89 (1H, d, J=2.7 Hz), 7.64 (1H, dd, J=2.4 Hz, J=9.0 Hz), 7.52-7.45 (1H, m), 7.36-7.30 (3H, m), 7.23-7.16 (1H, m), 5.31 (2H, s), 4.36-4.34 (1H, m), 4.25-4.22 (1H, m), 4.04-3.98 (1H, m), 3.84-3.77 (1H, m), 3.04-2.85 (3H, m), 2.28 (3H, s).

Example 3

Preparation of 4-(3-chloro-4-(3-fluorobenzyloxy)phenylamino)-6-(1-(2-ethylaminoethoxyimino)-2-butyn-1-yl)quinazoline (VI-4)

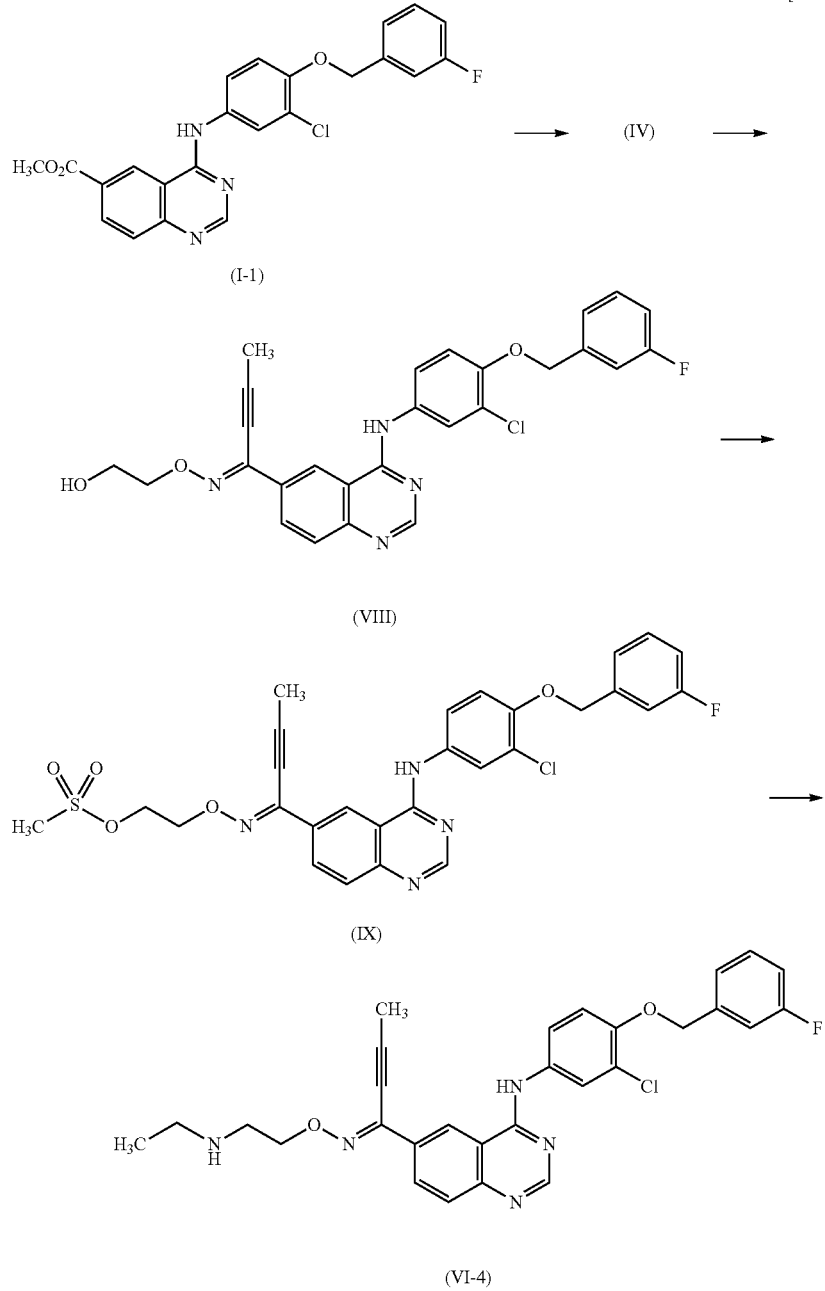

[Chemical formula 27]

(1) The compound (IV) was prepared according to the above Example 1.

(2) Preparation of 4-(3-chloro-4-(3-fluorobenzyloxy)phenylamino)-6-(1-(2-hydroxyethoxyimino)-2-butyn-1-yl)quinazoline (VIII)

To a solution of 4-(3-chloro-4-(3-fluorobenzyloxy)phenylamino)-6-(1-oxo-2-butyn-1-yl)quinazoline (IV) (10 g) in 1,4-dioxane (300 mL) was added 2-(acetoxy)ethoxyamine (1.5 equiv) and then 2 mol/L methane sulfonic acid aq. solution (28 mL) and stirred for 17 hr at 60° C. The reaction mixture was poured into saturated sodium hydrogen carbonate aq. solution and extracted with ethyl acetate. Organic layer was washed with water and dried over sodium sulfate. The filtrate was concentrated and the residue was recrystallized from hydrous ethanol-water, filtered and dried to give 4-(3-chloro-4-(3-fluorobenzyloxy)phenylamino)-6-(1-(2-hydroxyethoxyimino)-2-butyn-1-yl)quinazoline (VIII) (7.6 g) as a colorless solid.

$^1$H-NMR (d$_6$-DMSO, δ): 10.07 (1H, s), 8.74 (1H, s), 8.58 (1H, s), 8.22 (1H, d, J=8.8 Hz), 7.96 (1H, d, J=2.4 Hz), 7.80 (1H, d, J=8.8 Hz), 7.69 (1H, dd, J=2.4 Hz, J=8.8 Hz), 7.50-7.45 (1H, m), 7.35-7.24 (3H, m), 7.20-7.16 (1H, m), 5.27 (2H, s), 4.79 (1H, t. J=5.6 Hz), 4.29 (2H, t. J=5.6 Hz), 3.75 (2H, dd, J=5.2 Hz, J=10.4 Hz), 2.26 (3H, s).

(3) Preparation of 4-(3-chloro-4-(3-fluorobenzyloxy)phenylamino)-6-(1-(2-sulphonyloxyethoxyimino)-2-butyn-1-yl)quinazoline (IX)

To a solution of 4-(3-chloro-4-(3-fluorobenzyloxy)phenylamino)-6-(1-(2-hydroxyethoxyimino)-2-butyn-1-yl)quinazoline (VIII) (7.6 g) in tetrahydrofuran (150 mL) was added triethylamine (4.19 mL) and methanesulfonyl chloride (2.33 mL) and stirred for 3.5 hr. After the reaction was completed, the reaction mixture was poured into water and sodium hydrogen carbonate aq. solution was added to it. The mixture was extracted with ethyl acetate and the organic layer was dried over sodium sulfate and the filtrate was concentrated. Ethyl acetate was added to the residue and stood still at room temperature to give crystalline, and then diluted with hexane. The formed crystalline was filtered to give 4-(3-chloro-4-(3-fluorobenzyloxy)phenylamino)-6-(1-(2-sulphonyloxyethoxyimino)-2-butyn-1-yl)quinazoline (IX) (7.66 g) as light yellow crystalline.

$^1$H-NMR (d$_6$-DMSO, δ): 10.07 (1H, s), 8.77 (1H, s), 8.60 (1H, s), 8.24 (1H, d, J=8.8 Hz), 7.97 (1H, d, J=2.4 Hz), 7.81 (1H, d, J=8.8 Hz), 7.69 (1H, dd, J=2.4 Hz, J=8.8 Hz), 7.51-7.45 (1H, m), 7.35-7.27 (3H, m), 7.21-7.17 (1H, m), 5.27 (2H, s), 4.58 (2H, t. J=4.8 Hz), 4.54 (2H, t. J=4.8 Hz), 3.24 (3H, s), 2.27 (3H, s).

(4) Preparation of 4-(3-chloro-4-(3-fluorobenzyloxy)phenylamino)-6-(1-(2-ethylaminoethoxyimino)-2-butyn-1-yl)quinazoline (VI-4)

To a solution of 4-(3-chloro-4-(3-fluorobenzyloxy)phenylamino)-6-(1-(2-sulphonyloxyethoxyimino)-2-butyn-1-yl)quinazoline (IX) (100 mg) in N,N-dimethylformamide (3 mL) was added 70% ethylamine aq. solution (160 μl) and stirred for 14 hr at 60° C. Water was added to the reaction mixture and extracted with ethyl acetate. The organic layer was dried over magnesium sulfate, the filtrate was concentrated and the residue was purified using an amino column (eluting with ethyl acetate) to give 4-(3-chloro-4-(3-fluorobenzyloxy)phenylamino)-6-(1-(2-ethylaminoethoxyimino)-2-butyn-1-yl)quinazoline (VI-4) (53 mg) as a colorless solid.

$^1$H-NMR (d$_6$-DMSO, δ): 10.08 (1H, s), 8.74 (1H, s), 8.59 (1H, s), 8.21 (1H, d, J=8.4 Hz), 7.96 (1H, s), 7.80 (1H, d, J=8.8 Hz), 7.69 (1H, d, J=8.0 Hz), 7.51-7.45 (1H, m), 7.35-7.27 (3H, m), 7.21-7.16 (1H, m), 5.27 (2H, s), 4.31 (2H, t. J=5.6 Hz), 2.89 (2H, t, J=6.0 Hz), 2.61 (2H, q, J=7.2 Hz), 2.26 (3H, s), 1.02 (3H, t, J=7.6 Hz).

For above amination, commercially available amines or amines or a salt thereof prepared according to the methods described in J. Syn. Org. Chem., Jpn., 2001, 59: 779-789, Tetrahedron Lett., 1995, 36: 6373-6374, Synlett, 1999: 1301-1303, or Tetrahedron, 2002, 58: 6267-6276 can be used.

Example 4

[Chemical formula 28]

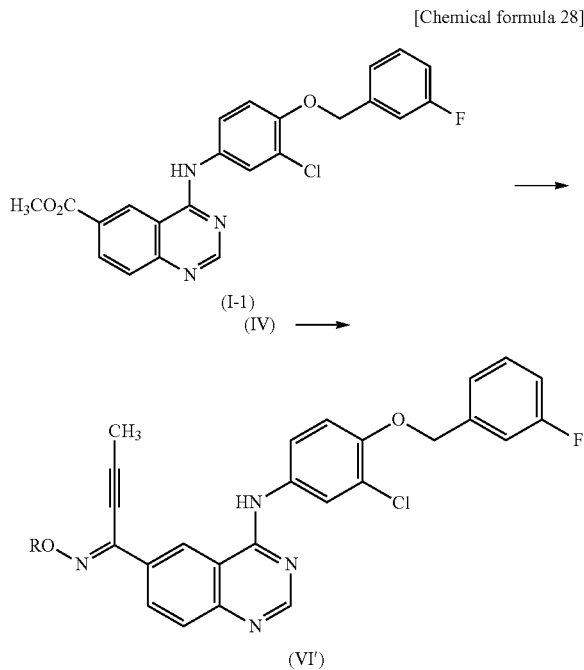

The compounds (VI-5)-(VI-20) were prepared according to the same manner as those of the above Examples.

TABLE 3

| Compound No. | R | $^1$H-NMR(d$_6$-DMSO) |
|---|---|---|
| (VI-5) | ![structure] HO-CH(CH₃)-CH₂-NH-CH₂-CH₂-O-N= | 10.08(1H, s), 8.75(1H, s), 8.68(1H, s), 8.22(1H, d, J = 8.8 Hz), 7.79(1H, s), 7.80(1H, d, J = 7.2 Hz), 7.70 (1H, d, J = 8.8 Hz), 7.50-7.45(1H, m), 7.35-7.27(3H, m), 7.18(1H, t, J = 8.8 Hz), 5.27(2H, s), 4.34(2H, t, J = 5.6 Hz), 3.35-3.32(2H, m), 2.92(2H, t, J = 5.6 Hz), 2.65-2.61(1H, m), 2.26(3H, s), 1.75-1.70(1H, bs), 0.84(3H, d, J = 5.6 Hz). |

TABLE 3-continued

| Compound No. | R | ¹H-NMR(d₆-DMSO) |
|---|---|---|
| (VI-6) | [structure: H₃C-O-CH₂CH₂-N(CH₃)-CH₂CH₂-O-N=C(CH₃)-C≡C-CH₃] | 10.09(1H, s), 8.58(1H, s), 8.22(1H, dd, J = 8.7 Hz, 1.8 Hz), 7.95(1H, d, J = 2.7 Hz), 7.80(1H, d, J = 9.0 Hz), 7.68(1H, dd, J = 8.7 Hz, 2.7 Hz), 7.51-7.44 (1H, m), 7.35-7.16(4H, m), 3.22(3H, s), 2.77(2H, t, J = 5.7 Hz), 2.60(2H, t, J = 5.7 Hz), 2.29(3H, s), 2.24 (3H, s). |
| (VI-7) | [structure: H₃C-O-CH₂CH₂-N(CH₂CH₃)-CH₂CH₂-O-N=C(CH₃)-C≡C-CH₃] | 10.09(1H, bs), 8.74(1H, s), 8.58(1H, s), 7.96(1H, d, J = 2.1 Hz), 7.80(1H, d, J = 8.7 Hz), 7.68(1H, d, J = 9.0 Hz), 7.48 (1H, dd, J = 8.1 Hz), 7.35-7.26(3H, m), 7.19(1H, t, J = 8.1 Hz), 5.27(2H, s), 4.32(2H, t, J = 6.0 Hz), 3.23(3H, s), 2.85(2H, t, J = 6.0 Hz), 2.87-2.59 (4H, m), 2.24(3H, s), 0.98(3H, t, J = 7.2 Hz). |
| (VI-8) | [structure: HO-CH₂CH₂-N(CH₃)-CH₂CH₂-O-N=C(CH₃)-C≡C-CH₃] | (二塩酸塩) 10.70(1H, brs), 9.92(1H, brs), 8.94(1H, s), 8.69(1H, s), 8.30(1H, d, J = 12), 7.95-7.94(1H, m), 7.86(1H, d, J = 12), 7.71-7.68(1H, m), 7.52-7.44(1H, m), 7.35-7.28(3H, m), 7.22-7.15(1H, m), 5.40(1H, br), 5.30(2H, s), 4.74-4.60(2H, m), 3.83-3.75(2H, m), 3.70-3.55(2H, m), 2.92(3H, s), 2.28(3H, s) |
| (VI-9) | [structure: H₃C-NH-CH₂CH₂CH₂-O-N=C(CH₃)-C≡C-CH₃] | 10.09(1H, s), 8.75(1H, s), 8.59(1H, s), 8.22(1H, d, J = 8.7 Hz), 7.95(1H, d, J = 2.1 Hz), 7.81 (1H, d, J = 9.0 Hz), 7.69(1H, d, J = 8.7 Hz), 7.51-7.34 (1H, m), 7.34-7.26(2H, m), 7.21-7.16(1H, m), 5.27(2H, s), 4.34(2H, t, J = 6.3 Hz), 2.96(2H, t,, J = 6.9 Hz), 2.56(3H, s), 2.26(3H, s). |
| (VI-10) | [structure: azetidine-O-N=C(CH₃)-C≡C-CH₃] | 10.4(1H, s), 9.06(1H, s), 8.59(1H, s), 8.30(1H, d J = 8 Hz), 8.01(1H, s), 7.81(1H, d, J = 8.8 Hz), 7.74(1H, d, J = 8.8 Hz), 7.44-7.50(1H, m), 7.24-7.36(3H, m), 7.18(1H, t, J = 7.2 Hz), 5.27(2H, s), 4.21-4.36(4H, m), 3.98-4.04(1H, m), 2.25(3H, s) |

TABLE 4

| Compound No. | R | ¹H-NMR(d₆-DMSO) |
|---|---|---|
| (VI-11) | pyrrolidin-2-ylmethyl-O-N= group with CH₃/alkyne | 10.08(1H, bs), 8.74(1H, s), 8.56(1H, s), 8.21(1H, d, J = 8.0 Hz), 7.93(1H, s), 7.79(1H, d, J = 8.8 Hz), 7.67-7.65(1H, m), 7.50-7.40(1H, m), 7.33-7.24(2H, m), 7.20-7.12(1H, m), 5.25(2H, s), 4.36-4.30(1H, m), 4.22-4.17(1H, m), 4.08-3.92(2H, m), 2.98(2H, bs), 2.24(3H, s), 2.00-1.90(1H, m), 1.80-1.70(2H, m), 1.62-1.52(1H, m) |
| (VI-12) | 4-hydroxypyrrolidin-2-ylmethyl-O-N= group | 10.45(1H, s), 8.92(1H, s), 8.65(1H, s), 8.31(1H, d, J = 8.4 Hz), 7.97(1H, s), 7.77(1H, d, J = 8.8 Hz), 7.71 (1H, d, J = 9.2 Hz), 7.51-7.45(1H, m), 7.35-7.28(2H, m), 7.19(1H, t, J = 8.4 Hz), 5.28(2H, s), 4.56-4.47(3H, m), 4.15(1H, bs), 3.60(1H, bs), 3.12(1H, bs), 2.28(3H, s), 2.09(1H, dd, J = 13.2 Hz, J = 6.0 Hz), 1.86 2-1.8(1H, m). |
| (VI-13) | 4-hydroxypyrrolidin-2-ylmethyl-O-N= group (diastereomer) | 10.08(1H, s), 8.75(1H, s), 8.59(1H, s), 8.22(1H, d, J = 8.8 Hz), 7.97(1H, s), 7.80(1H, d, J = 8.8 Hz), 7.69 (1H, d, J = 8.0 Hz), 7.51-7.45(1H, m), 7.35-7.27(m, 3H), 7.20-7.17(1H, m), 5.27(2H, s), 4.67(1H, bs), 4.29-4.19(3H, m), 3.45-4.40(1H, m), 2.88(1H, dd, J = 11.2 Hz, J = 5.6 Hz), 2.70(1H. dd, J = 11.0, J = 3.6 Hz), 2.27(3H, s), 2.10-2.02(1H, m), 1.46-1.39(1H, m). |
| (VI-14) | morpholin-3-ylmethyl-O-N= group | 10.09(1H, bs), 8.75(1H, s), 8.58(1H, s), 8.20(1H, d, J = 8.7 Hz), 7.95(1H, d, J = 2.1 Hz), 7.80(1H, d, J = 8.7 Hz), 7.68(1H, d, J = 9.0 Hz), 7.51-7.44(1H, m), 7.35-7.26(3H, m), 7.21-7.16(1H, m), 5.27(2H, s), 4.20-4.09(2H, m), 3.79(1H, dd, J = 2.7 Hz, J = 10.8 Hz), 3.68-3.64(1H, m), 3.13-3.08(1H, m), 2.82-2.71(3H, m), 2.26(3H, s). |
| (VI-15) | morpholin-3-ylmethyl-O-N= group (enantiomer) | 10.11(1H, bs), 8.74(1H, s), 8.57(1H, s), 8.22-8.19 (1H, m), 7.96(1H, m), 7.80(1H, d, J = 9.0 Hz), 7.69-7.66(1H, m), 7.51-7.44(1H, m), 7.35-7.26(3H, m), 7.21-7.16(1H, m), 5.27(2H, s), 4.20-4.09(2H, m), 3.79 (1H, dd, J = 3.0 Hz, J = 10.8 Hz), 3.68-3.64(1H, m), 3.25-3.18(1H, m), 3.13-3.05(1H, m), 2.82-2.71(2H, m), 2.26(3H, s). |
| (VI-16) | piperazin-2-ylmethyl-O-N= group | 10.09(1H, brs), 8.74(1H, s), 8.59(1H, s), 8.21(1H, d, 9.0 Hz), 7.96(1H, s), 7.79(1H, d, J = 9.0 Hz) 7.68 (1H, d, J = 9.0 Hz), 7.49-7.44(1H, m), 7.34-7.22(3H, m), 7.19-7.15(1H, m), 5.27(2H, s), 4.11(2H, d, J = 4.8 Hz), 2.95-2.50(6H, m), 2.34-2.26(4H, m) |

TABLE 5

| Compound No. | R | $^1$H-NMR($d_6$-DMSO) |
|---|---|---|
| (VI-17) | morpholinoethyl-O-N=C(CH$_3$)-C≡C- (2-(morpholin-4-yl)ethoxyimino group with methyl and alkyne) | (E/Z mixture) 10.09(1H, s, major), 10.00(1H, s, minor), 8.74(1H, s, major), 8.59(1H, s), 8.22(1H, d, J = 9 Hz, major), 7.94-8.02(1H, m), 7.64-7.82(2H, m), 7.44-7.52 (1H, m), 7.16-7.36(4H, m), 5.27(2H, s), 4.32-4.43(2H, m), 3.56-3.62(4H, m), 2.66-2.74(2H, m), 2.34(3H, s, minor), 2.25(3H, s, major) |
| (VI-18) | pyrrolidin-1-yl-ethyl-O-N=C(CH$_3$)-C≡C- | 10.08(1H, s), 8.74(1H, s), 8.58(1H, s), 8.22(1H, d, J = 8.4 Hz), 7.96(1H, brs), 7.80(1H, d, J = 8.4 Hz), 7.68(1H, d, J = 9.6 Hz), 7.43-7.52(1H, m), 7.14-7.36(4H, m), 5.27 (2H, s), 4.37(2H, t, J = 6.0 Hz), 2.80(2H, t, J = 6.0 Hz), 2.25(3H, s), 1.69(4H, brs), 1.24(4H, brs) |
| (VI-19) | H$_3$C-NH-CH$_2$CH$_2$-O-N=C(CH$_3$)-C≡C- | 10.10(1H, s), 8.76(1H, s), 8.60(1H, s), 8.25(1H, d, J = 8.7 Hz), 7.96(1H, brs), 7.82(1H, d, J = 9.0 Hz), 7.69(1H, d, J = 9.0 Hz), 7.43-7.52(1H, m), 7.14-7.36(4H, m), 5.28 (2H, s), 4.43(2H, brs), 2.98(2H, brs), 2.54(3H, s), 2.27(3H, brs), 1.60(1H, s) |
| (VI-20) | cyclohexyl-NH-CH$_2$CH$_2$-O-N=C(CH$_3$)-C≡C- | 10.10(1H, s), 8.77(1H, s), 8.60(1H, s), 8.25(1H, d, J = 8.7 Hz), 7.95(1H, brs), 7.82(1H, d, J = 9.6 Hz), 7.69(1H, d, J = 9.3 Hz), 7.43-7.52(1H, m), 7.14-7.36(4H, m), 5.28 (2H, s), 4.45(2H, brs), 2.91(2H, brs), 2.27(3H, s), 2.00(2H, brs), 1.73(2H, brs), 1.60(1H, brs), 1.23(7H, brs) |

Test Example 1

Stability Test of the Crystalline Form

The crystalline form of the compound (IV) monohydrate was sealed in a glass vial and allowed it to stand for 20 days to determine the quality change before and after the test. Under heating at 50° C. (for 21 hr) or 80° C. (for 9 hr) were also conducted.

The quality degradation was not seen for the crystalline form of the compound (IV) monohydrate after 20 days and neither at 50° C. nor 80° C. Table 6 shows data of remaining ratio of the crystalline form of the compound (IV) monohydrate at rt (ca. 22° C.), Table 7 shows remaining ratio of the crystalline form of the compound (IV) monohydrate at rt (ca. 50° C.), and Table 8 shows remaining ratio of the crystalline form of the compound (IV) monohydrate at rt (ca. 80° C.).

HPLC condition: Column Unison UK-C18 3 μm;

Mobile phase: 0.1% trifuluoroacetic acid aq. in acetnitrile;

Column temperature: 30° C.

Detector: UV spectrophotometer (254 nm)

TABLE 6

| | Retention Time (min) | | | | | | | | | |
|---|---|---|---|---|---|---|---|---|---|---|
| Time | 4.3 | 5.2 | 5.5 | 5.7 | 6.6 | 7.7 | 8.1 | 10.2 | 15.3 | 16.3 |
| Control | 0.18 | 0.02 | 0.02 | 0.04 | 0.02 | 0.14 | 0.03 | 99.1 | 0.07 | 0.02 |
| 20 days | 0.18 | 0.02 | 0.01 | 0.02 | ND | 0.13 | 0.02 | 99.3 | 0.04 | 0.01 |

TABLE 7

| Time | Retention Time (min) | | | | | | | | |
|---|---|---|---|---|---|---|---|---|---|
| | 4.3 | 5.2 | 5.5 | 5.7 | 6.6 | 7.7 | 8.1 | 10.2 | 15.3 | 16.3 |
| Control | 0.15 | 0.14 | 0.01 | 0.03 | 0.06 | 0.04 | 0.04 | 99.4 | 0.04 | ND |
| 15 h | 0.16 | 0.13 | 0.02 | 0.05 | 0.05 | 0.05 | 0.07 | 99.2 | 0.06 | 0.03 |
| 21 h | 0.18 | 0.15 | 0.01 | 0.03 | ND | 0.04 | 0.06 | 99.1 | 0.06 | 0.07 |

TABLE 8

| Time | Retention Time (min) | | | | | | | | |
|---|---|---|---|---|---|---|---|---|---|
| | 4.3 | 5.2 | 5.5 | 5.7 | 6.6 | 7.7 | 8.1 | 10.2 | 15.3 | 16.3 |
| Control | 0.25 | 0.18 | | 0.01 | 0.06 | 0.04 | 0.07 | 99.1 | 0.04 | 0.02 |
| 3 h | 0.25 | 0.16 | 0.01 | 0.03 | ND | 0.04 | 0.06 | 99.1 | 0.05 | 0.04 |
| 9 h | 0.17 | 0.13 | 0.01 | 0.03 | ND | 0.04 | 0.05 | 99.1 | 0.05 | 0.07 |

Test Example 2

Stability Test of the Crystalline Form

The crystalline form of the compound (IV) nonhydrate or monohydrate thereof was placed in doubled plastic bags sealed by convex and subjected to long term stability test (temperature: 25° C.±2° C., humidity: 65%±5% RH, light: shielded) or accelerated test (temperature: 40° C.±2° C., humidity: 75%±5% RH, light: shielded) to test the stability. Stability was tested by measuring remaining ratio of the compound (IV) by HPLC using absolute calibration curve method in every 2 weeks to 3 months from the beginning of the test. For example, following HPLC conditions are used:

HPLC condition: Column Unison UK-C18 3 μm;
Mobile phase: 0.1% trifuluoroacetic acid aq./0.1% trifuluoroacetic acid in acetnitrile;
Column temperature: 15° C.
Detector: UV spectrophotometer (355 nm)

INDUSTRIAL APPLICABILITY

According to the continuous preparation process of the present invention, the compound (III) which is useful as a synthetic intermediate of a dual tyrosine kinase inhibitor is prepared substantially as one step.

The invention claimed is:

1. A process for preparing a compound represented by the formula (III):

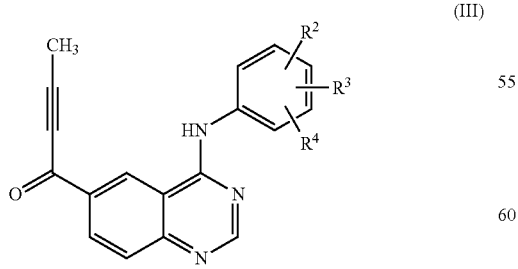

(III)

wherein $R^2$ is a hydrogen atom, halogen, substituted or unsubstituted alkyloxy, substituted or unsubstituted alkenyloxy, substituted or unsubstituted alkynyloxy or a group represented by the formula: —Y—$R^y$ wherein —Y— is —O—, —S—, —$SO_2$—, or alkylene which may be intervened with —O—, —S— or —N($R^z$)—; and $R^y$ is substituted or unsubstituted aryl or substituted or unsubstituted heteroaryl; $R^z$ is a hydrogen atom, substituted or unsubstituted alkyl, substituted or unsubstituted acyl, substituted or unsubstituted alkyloxycarbonyl, substituted or unsubstituted alkenyloxycarbonyl or substituted or unsubstituted aralkyloxycarbonyl;

$R^3$ and $R^4$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino;

a salt, or a solvate thereof;

comprising:

Reaction A, in which a compound represented by the formula (I):

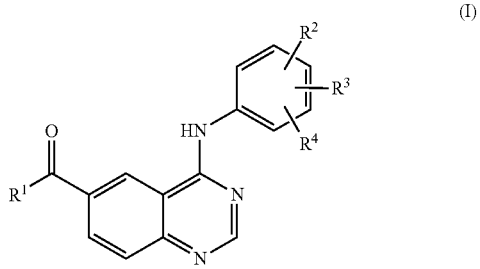

(I)

wherein $R^1$ is a group represented by the formula: —O—$R^x$ or —S—$R^x$ wherein $R^x$ is substituted or unsubstituted alkyl, substituted or unsubstituted alkenyl, substituted or unsubstituted alkynyl, substituted or unsubstituted aryl or a group represented by the formula (II):

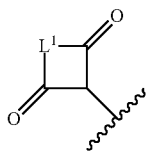

(II)

wherein $L^1$ is substituted or unsubstituted C2-C3 alkylene; $R^2$, $R^3$ and $R^4$ are as defined above, is reacted with 1.0 to 1.5 equivalent of a compound represented by the formula: $(R^bO—)N(—R^a)H$ wherein $R^a$ and $R^b$ are each independently substituted or unsubstituted C1-C3 alkyl; or a salt thereof, and 3 to 4 equivalent of one or more metallic reagent(s) selected from the group consisting of Grignard reagent, sodium hydride, alkyllithium, alkenyllithium, alkynyllithium, phenyllithium, and lithium amide;

and reaction B, in which a product of reaction A is reacted with 1-propynyl metal acetylide;

are carried out substantially as one step by continuously conducting these two reactions.

2. The process according to claim 1:

wherein $R^2$ is a group represented by the formula: —Y—$R^y$ wherein —Y— is alkylene which may be intervened with —O—; and $R^y$ is phenyl unsubstituted or substituted with a substituent selected from a substituent group p consisting of [halogen, carboxy, alkyl, haloalkyl, hydroxyalkyl, alkyloxy, alkyloxycarbonyl and substituted or unsubstituted amino], pyridyl unsubstituted or substituted with a substituent selected from a substituent group p, furyl unsubstituted or substituted with a substituent selected from a substituent group p, thienyl unsubstituted or substituted with a substituent selected from a substituent group p, thiazolyl unsubstituted or substituted with a substituent selected from a substituent group p, or oxazolyl unsubstituted or substituted with a substituent selected from a substituent group p;

$R^3$ is substituted or unsubstituted alkynyl, substituted or unsubstituted alkyloxy or halogen; and $R^4$ is a hydrogen atom.

3. The process according to claim 1, wherein the compound represented by the formula (III), a salt or a solvate thereof is a crystalline form.

4. The process according to claim 1, wherein the compound represented by the formula (III) is a compound represented by the formula (IV):

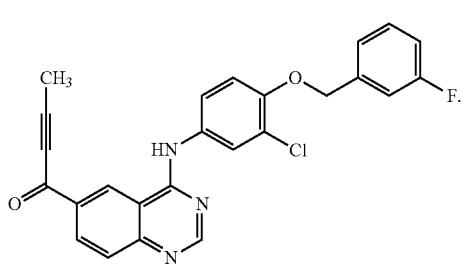

(IV)

5. The process according to claim 4, comprising a step wherein the compound represented by the formula (IV) is recrystallized from an organic solvent.

6. A process for preparing a compound represented by the formula (VI):

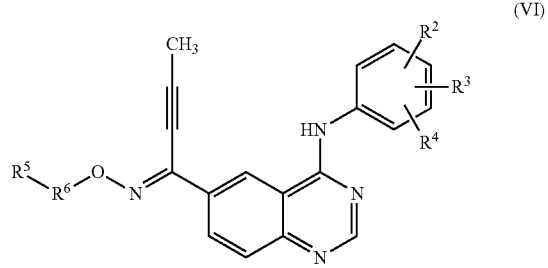

(VI)

wherein $R^2$, $R^3$ and $R^4$ are as defined in claim 1 and $R^5$ is substituted or unsubstituted aryl, substituted or unsubstituted heteroaryl, substituted or unsubstituted heterocyclyl or substituted or unsubstituted amino, and $R^6$ is substituted or unsubstituted C1-3 alkylene, a salt or a solvate thereof;

wherein:

the compound represented by the formula (III), a salt or a solvate thereof, which was prepared by the process according to claim 1, is reacted with a compound represented by the formula (V): $R^5$—$R^6$—O—$NH_2$, wherein $R^5$ and $R^6$ are as defined above.

7. A process for preparing a compound represented by the formula (VI'):

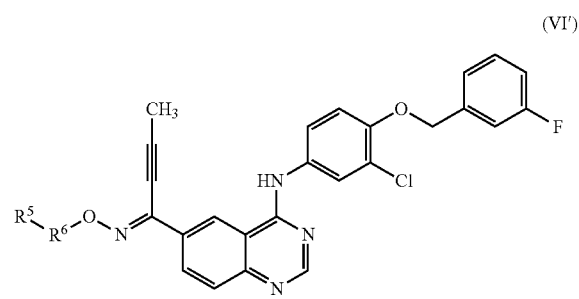

(VI')

wherein $R^5$ is substituted or unsubstituted aryl, substituted or unsubstituted heteroaryl, substituted or unsubstituted heterocyclyl or substituted or unsubstituted amino, and $R^6$ is substituted or unsubstituted C1-3 alkylene, a salt or a solvate thereof, wherein:

the compound represented by the formula (IV), a salt or a solvate thereof, which was prepared by the process according to claim 4, is reacted with the compound represented by the formula (V): $R^5$—$R^6$—O—$NH_2$, wherein $R^5$ and $R^6$ are as defined above.

8. The process according to claim 2, wherein the compound represented by the formula (III), a salt or a solvate thereof is a crystalline form.

9. The process according to claim 2, wherein the compound represented by the formula (III) is a compound represented by the formula (IV):

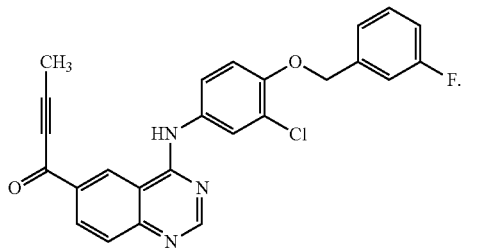

(IV)

10. The process according to claim 3, wherein the compound represented by the formula (III) is a compound represented by the formula (IV):

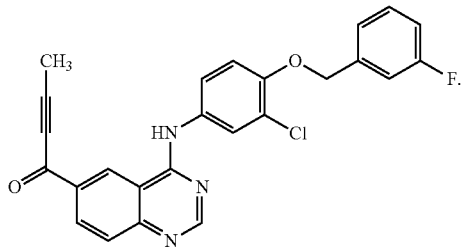

(IV)

11. The process according to claim 6:
wherein $R^2$ is a group represented by the formula: —Y—$R^y$ wherein —Y— is alkylene which may be intervened with —O—; and $R^y$ is phenyl unsubstituted or substituted with a substituent selected from a substituent group p consisting of [halogen, carboxy, alkyl, haloalkyl, hydroxyalkyl, alkyloxy, alkyloxycarbonyl and substituted or unsubstituted amino], pyridyl unsubstituted or substituted with a substituent selected from a substituent group p, furyl unsubstituted or substituted with a substituent selected from a substituent group p, thienyl unsubstituted or substituted with a substituent selected from a substituent group p, thiazolyl unsubstituted or substituted with a substituent selected from a substituent group p, or oxazolyl unsubstituted or substituted with a substituent selected from a substituent group p;
$R^3$ is substituted or unsubstituted alkynyl, substituted or unsubstituted alkyloxy or halogen; and
$R^4$ is a hydrogen atom.

12. The process according to claim 6, wherein the compound represented by the formula (III), a salt or a solvate thereof is a crystalline form.

13. A process for preparing a compound represented by the formula (VI'):

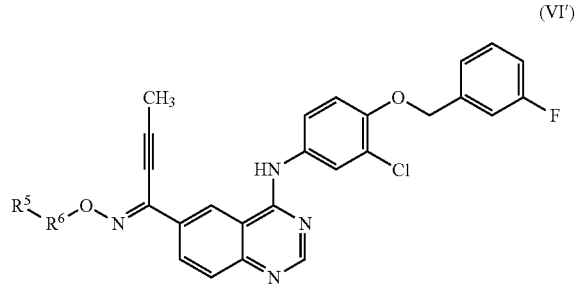

(VI')

wherein $R^5$ is substituted or unsubstituted aryl, substituted or unsubstituted heteroaryl, substituted or unsubstituted heterocyclyl or substituted or unsubstituted amino, and $R^6$ is substituted or unsubstituted C1-3 alkylene, a salt or a solvate thereof, wherein:
the compound represented by the formula (IV), a salt or a solvate thereof, which was prepared by the process according to claim 5,
is reacted with the compound represented by the formula (V): $R^5$—$R^6$—O—$NH_2$, wherein $R^5$ and $R^6$ are as defined above.

* * * * *